US012781283B2

(12) United States Patent
Xiao et al.

(10) Patent No.: US 12,781,283 B2
(45) Date of Patent: Nov. 3, 2026

(54) USE OF TMED8 GENE IN PREPARATION OF DRUG AND DIAGNOSTIC KIT FOR PANCREATIC CANCER

(71) Applicant: AFFILIATED HOSPITAL OF NANTONG UNIVERSITY, Nantong (CN)

(72) Inventors: Mingbing Xiao, Nantong (CN); Tong Wu, Nantong (CN); Xingjuan Fan, Nantong (CN); Jiahai Shi, Nantong (CN); Wenjie Zheng, Nantong (CN); Wenkai Ni, Nantong (CN); Chengqi Guan, Nantong (CN); Ziwei Chen, Nantong (CN)

(73) Assignee: AFFILIATED HOSPITAL OF NANTONG UNIVERSITY, Nantong (CN)

( * ) Notice: Subject to any disclaimer, the term of this patent is extended or adjusted under 35 U.S.C. 154(b) by 381 days.

(21) Appl. No.: 18/603,164

(22) Filed: Mar. 12, 2024

(65) Prior Publication Data

US 2025/0003006 A1 Jan. 2, 2025

(30) Foreign Application Priority Data

Jun. 27, 2023 (CN) ......................... 202310770107.3

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

2023/0398130 A1* 12/2023 Mead .................. A61K 31/593

FOREIGN PATENT DOCUMENTS

WO WO-2023183893 A1 * 9/2023 ............ C12N 9/226

* cited by examiner

*Primary Examiner* — Anne M. Gussow
*Assistant Examiner* — Mindy G Brown
(74) *Attorney, Agent, or Firm* — Bochner PLLC; Andrew D. Bochner

(57) ABSTRACT

The present disclosure provides use of a transmembrane emp24 domain 8 (TMED8) gene in preparation of a drug and a diagnostic kit for pancreatic cancer, and belongs to the technical field of precision tumor medicine. In the present disclosure, it is found that up-regulating an expression level of the TMED8 gene has significantly inhibited migration and proliferation of pancreatic cancer cells, and then promoted apoptosis of the pancreatic cancer cells; the TMED8 gene is further found to be related to a mitogen-activated protein kinase (MAPK) signaling pathway. Therefore, the TMED8 gene may be used as an effective target for gene diagnosis and treatment of the pancreatic cancer.

1 Claim, 20 Drawing Sheets

Specification includes a Sequence Listing.

N1

T1 Highly-differentiated PAAD

N2

T2 Moderately-differentiated PAAD

N3

T3 Poorly-differentiated PAAD

B

B pLV3-CMV TMED8(human)-3xFLAG-EF1a-CopGFP-Puro
9244bp

USE OF TMED8 GENE IN PREPARATION OF DRUG AND DIAGNOSTIC KIT FOR PANCREATIC CANCER

CROSS REFERENCE TO RELATED APPLICATION

This patent application claims the benefit and priority of Chinese Patent Application No. 2023107701073 filed with the China National Intellectual Property Administration on Jun. 27, 2023, the disclosure of which is incorporated by reference herein in its entirety as part of the present application.

REFERENCE TO SEQUENCE LISTING

A computer readable XML file entitled "SEQUENCE LISTING", that was created on Jan. 24, 2024, with a file size of about 14516 bytes, contains the sequence listing for this application, has been filed with this application, and is hereby incorporated by reference in its entirety.

TECHNICAL FIELD

The present disclosure belongs to the technical field of precision tumor medicine, and specifically relates to use of a transmembrane emp24 domain 8 (TMED8) gene in preparation of a drug and a diagnostic kit for pancreatic cancer.

BACKGROUND

Pancreatic cancer (PC), as an extremely-common and highly-malignant tumor with difficult early diagnosis, easy metastasis, rapid progression, and extremely poor prognosis, is a leading cause of cancer death worldwide. North America, Europe and Australia have the highest incidence rate of pancreatic cancer. As the world's population ages, smoking, obesity, diabetes, and alcohol consumption have become more prevalent in many parts of the world, resulting in a sharp increase in the incidence of pancreatic cancer. However, a relative contribution of these risk factors varies globally due to differences in underlying prevalence and prevention strategies. Inherited genetic factors, although not directly modifiable, are an important component of pancreatic cancer risk, and include pathogenic variants in inherited cancer genes, genes associated with hereditary pancreatitis, and common variants identified in genome-wide association study (GWAS). Identifying genetic changes in cancer not only provides insight into the cause of this cancer but also provides the opportunity to guide early detection strategies. The pancreatic cancer has no obvious symptoms in its early stages, making it difficult to detect and diagnose in time. Tumor markers that are currently commonly used in clinical practice, such as CA199 and CEA, have poor sensitivity and specificity for the early diagnosis of pancreatic cancer. Once diagnosed, most patients with pancreatic cancer are already in the intermediate and advanced stages. In addition to radical surgical resection, adjuvant radiotherapy and chemotherapy and other methods show extremely limited improvement in prognosis. Therefore, it is of great significance to explore and discover early markers and effective therapeutic targets with greater sensitivity and specificity.

Transmembrane emp24 domain family (TMED family) consists of type I single-channel transmembrane proteins, is found in all eukaryotic organisms, and plays a role in human development and disease that cannot be ignored. The TMED is an important transporter in the secretory pathway. Once a protein transport pathway controlled by TMED is abnormal, there may be occurrence of various diseases including congenital malformations, diabetes, and cancer. Previous studies have shown that abnormal expression of TMED proteins is generally closely related to liver diseases, pancreatic diseases, and immune system disorders. The TMED proteins may form a secretory loop during the development of diseases, maintain a normal shape of cells and intracellular organelles, circulate and transport a variety of important cargo components between organelles, and achieve the communication between organelles. As a result, the TMED proteins continuously regulate a disease process, and especially play an important role in the proliferation and differentiation of malignant tumor cells.

TMED8 (NCBI Gene: 283578), one of the important members in the TMED family, is located between bases 77,335,021 to 77,377,094 of chromosome 14, has a molecular weight of approximately 55 kDa, and can be expressed in both the nucleus and cytoplasm. There are currently no literature reports on a relationship between the TMED8 and human diseases and normal physiological functions.

SUMMARY

A purpose of the present disclosure is to provide use of a TMED8 gene in preparation of a drug and a diagnostic kit for pancreatic cancer. The present disclosure specifically provides use of the TMED8 gene in preparation of a kit for disease diagnosis, as well as use of the TMED8 gene in preparation of a drug for treating a tumor.

The present disclosure provides use of a reagent for detecting an expression level of a TMED8 gene in preparation of a product for diagnosing a disease.

In one embodiment, the reagent includes a reagent for detecting an expression level of an mRNA or a protein of the TMED8 gene.

In one embodiment, a method for detecting the expression level of the TMED8 gene is at least one selected from the group consisting of immunohistochemistry, Western Blot, and real-time fluorescence quantitative PCR.

In one embodiment, the disease includes a tumor.

The present disclosure further provides a kit for diagnosing a tumor, including at least one of the following reagents: a reagent for detecting an expression level of a TMED8 protein using immunohistochemistry, a reagent for detecting the expression level of the TMED8 protein using Western Blot, and a primer pair for detecting an expression level of a TMED8 gene and/or an mRNA using real-time fluorescence quantitative PCR.

In one embodiment, the tumor includes pancreatic cancer.

The present disclosure further provides use of a reagent for increasing an expression level of a TMED8 gene in preparation of a product for treating a disease.

In one embodiment, the reagent is at least one selected from the group consisting of an agonist of the TMED8 gene, an analog of the TMED8 gene, and an agent for overexpressing the TMED8 gene.

The present disclosure further provides a drug for treating a tumor, including an agent for increasing an expression level of an endogenous TMED8 gene or an exogenous TMED8 gene.

In one embodiment, the treating includes at least one of the following: inhibiting tumor cell migration, inhibiting tumor cell proliferation, promoting tumor cell apoptosis, and inhibiting mitogen-activated protein kinase (MAPK) signaling pathway activation.

Beneficial effects: in the present disclosure, expression of the TMED8 gene in pancreatic cancer is detected using immunohistochemistry by preparing a pancreatic cancer tissue chip. The results have showed that the expression level of the TMED8 gene in a pancreatic cancer tumor tissue is significantly higher than that in tissues adjacent to cancer. In addition, a stably-transfected cell line of pancreatic cancer overexpressing TMED8 gene is established, and the influence of TMED8 gene on the biological behavior of pancreatic cancer cells is explored through in vivo and in vitro experiments such as qRT-PCR, Western Blot, cell scratching, CCK8, Transwell, flow cytometry, and subcutaneous tumor formation in nude mice. It is found that up-regulating an expression level of the TMED8 gene has significantly inhibited migration and proliferation of pancreatic cancer cells, and then promoted apoptosis of the pancreatic cancer cells; the TMED8 gene is further found to be related to a MAPK signaling pathway. Accordingly, the TMED8 gene may be used as an effective target for gene diagnosis and treatment of pancreatic cancer, and has an important application significance in the preparation of diagnostic kits and therapeutic drugs for precision medicine of the pancreatic cancer. The present disclosure for the first time explores an expression state in pancreatic cancer, an impact on the biological behavior of pancreatic cancer cells of the TMED8 gene, and a possible mechanism of action that is closely related to the MAPK signaling pathway. The TMED8 gene is expected to be used as a diagnostic kit as well as a therapeutic drug for pancreatic cancer, thus providing an effective support for early diagnosis and treatment of the pancreatic cancer.

BRIEF DESCRIPTION OF THE DRAWINGS

FIG. 1A to FIG. 1B represent the staining results of poorly-differentiated PC cancer and tissues adjacent to cancer; FIG. 1C to FIG. 1D represent the staining results of moderately-differentiated PC cancer and tissues adjacent to cancer; and FIG. 1E to FIG. 1F represent the staining results of highly-differentiated PC cancer and tissues adjacent to cancer;

DETAILED DESCRIPTION OF THE EMBODIMENTS

Figure 1A:
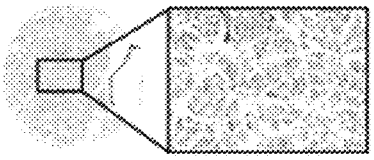
FIGS. 1A-F show the expression of TMED8 gene detected by immunohistochemistry (IHC) in pancreatic cancer and tissue chips adjacent to cancer; where representative sites are displayed.
Figure 1B:
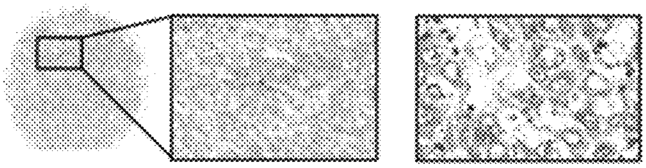
Figure 1C:
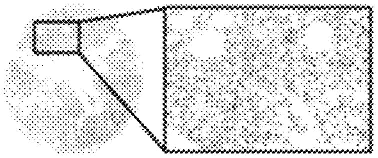
Figure 1D:
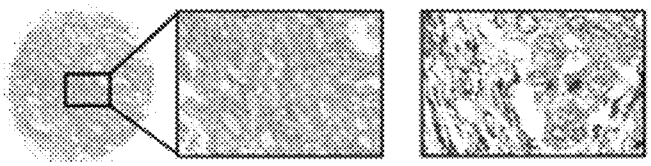
Figure 1E:
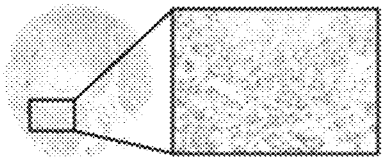
Figure 1F:
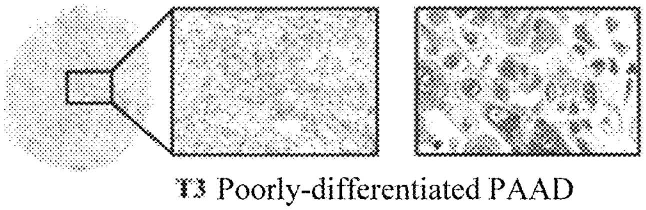

The present disclosure provides use of a reagent for detecting an expression level of a TMED8 gene in preparation of a product for diagnosing a disease.

In the examples of the present disclosure, a pancreatic cancer tissue chip is prepared based on a biological sample bank, and expression of the TMED8 gene in pancreatic cancer is detected using immunohistochemistry by preparing a pancreatic cancer tissue chip. The results have showed that the expression level of the TMED8 gene in a pancreatic cancer tumor tissue is significantly higher than that in tissues adjacent to cancer. Moreover, according to statistics, there is better prognosis of patients in a TMED8 gene high expression group, such that the TMED8 gene is used as a biomarker for the diagnosis of pancreatic cancer.

In the present disclosure, the reagent preferably includes a reagent for detecting an expression level of an mRNA or a protein of the TMED8 gene, and a detection method preferably includes at least one of the following: immunohistochemistry, Western Blot, and real-time fluorescence quantitative PCR. The disease preferably includes a tumor, more preferably pancreatic cancer.

The present disclosure further provides a kit for diagnosing a tumor, including at least one of the following reagents: a reagent for detecting an expression level of a TMED8 protein using immunohistochemistry, a reagent for detecting the expression level of the TMED8 protein using Western Blot, and a primer pair for detecting an mRNA expression level of the TMED8 gene by real-time fluorescence quantitative PCR. The primer sequences of the TMED8 gene and an internal reference 18S are shown in Table 1.

TABLE 1

Primer sequences

| Gene | Sequence | SEQ ID NO: |
|---|---|---|
| TMED8 | F: CCACCTCTGATGGCTCCT | 1 |
| | R: CTCACCACGCTTCACCAC | 2 |
| 18S | F: GGAGCCTGCGGCTTAATTTG | 3 |
| | R: CCACCCACGGAATCGAGAAA | 4 |

In the present invention, the tumor preferably includes pancreatic cancer.

The present disclosure further provides use of a reagent for increasing an expression level of a TMED8 gene in preparation of a product for treating a disease.

In the examples of the present disclosure, a stably-transfected cell line of pancreatic cancer overexpressing TMED8 gene is established, and the influence of TMED8 gene on the biological behavior of pancreatic cancer cells is explored through in vivo and in vitro experiments such as qRT-PCR, Western Blot, cell scratching, CCK8, Transwell, flow cytometry, and subcutaneous tumor formation in nude mice. It is found that up-regulating an expression level of the TMED8 gene has significantly inhibited migration and proliferation of pancreatic cancer cells, and then promoted apoptosis of the pancreatic cancer cells; the TMED8 gene is further found to be related to a MAPK signaling pathway.

Therefore, the TMED8 gene can be used as an effective target for gene treatment of the pancreatic cancer.

In the present disclosure, the reagent is preferably at least one selected from the group consisting of an agonist of the TMED8 gene, an analog of the TMED8 gene, and an agent for overexpressing the TMED8 gene.

In the present disclosure, a method for overexpressing the TMED8 gene preferably includes constructing an overexpression plasmid of the TMED8 gene, pLV3-CMV-TMED8 (human)-3×FLAG-EF1a-CopGFP-Puro, and the plasmid has a sequence shown in SEQ ID NO: 5.

The present disclosure further provides a drug for treating a tumor, including an agent for increasing an expression level of an endogenous TMED8 gene or an exogenous TMED8 gene.

In the present disclosure, a reagent for increasing an expression level of an endogenous TMED8 gene is preferably the same as the reagent for overexpressing the TMED8 gene, and will not be repeated here. The exogenous TMED8 gene is preferably the same as the agonist of the TMED8 gene and the analog of the TMED8 gene, and will not be repeated here. The treating includes preferably at least one of the following: inhibiting tumor cell migration, inhibiting tumor cell proliferation, promoting tumor cell apoptosis, and inhibiting MAPK signaling pathway activation.

To further illustrate the present disclosure, the use of the TMED8 gene in preparation of the drug and the diagnostic kit for pancreatic cancer provided by the present disclosure are described in detail below in connection with examples, but these examples should not be construed as limiting the claimed scope of the present disclosure.

In the examples of the present disclosure, the reagents and instruments used are common reagents and instruments in the field unless otherwise specified, and can be purchased from reagent stores:

1. The main reagents in the examples of the present disclosure include the following:

IHC detection kit (Servicebio, China); 4% paraformaldehyde fixation solution (Servicebio, China); PBS buffer (Servicebio, China); bovine serum albumin (BSA) powder (Solarbio Life Sciences, China); Triton X-100 (Solarbio Life Sciences, China); xylene (Sinopharm Group, China); hematoxylin staining solution (Beyotime, China); hematoxylin differentiation solution (Beyotime, China); absolute ethanol (Sinopharm Group, China); sodium citrate antigen retrieval solution (Beyotime, China); rabbit-derived anti-TMED8 antibody (Invitrogen, USA); rabbit-derived anti-Ki67 (Absin, China); HRP-labeled goat anti-rabbit secondary antibody (Abcam, USA); 95% ethanol (Sinopharm Group, China); DMEM basal medium (Cytiva, China); IMDM basal medium (Cytiva, China); RPMI basal medium (Cytiva, China); PBS basal buffer (Servicebio, China); fetal bovine serum (FBS) (Gibco, United States); serum-free cell cryopreservation medium (NCM Biotech, China); trypsin digestion solution containing EDTA (NCM Biotech, China); penicillin-streptomycin solution (NCM Biotech, China); tetracycline hydrochloride solution (Shanghai Sangon, China); puromycin (Sangon, USA); cell culture dish (Nest, China); Lipofectamine 2000 (Invitrogen, USA); 6-well plate, 96-well plate, 24-well plate (Nest, China); 8 μm transparent PET membrane for cell culture chamber (BD Falcon, USA); 1.5 mL, 4 mL, 10 mL centrifuge tubes, cell cryopreservation tube (Biosharp, USA); Trizol (Novizan, China); cell scraper (Nest, China); DEPC water (Shanghai Sangon, China); LC eight-tube strip (Roche, Switzerland); enzyme-free pipette tip, centrifuge tube (Biosharp, China); absolute ethanol (Sinopharm Group, China); isopropyl alcohol (Sinopharm Group, China); chloroform (Sinopharm Group, China); (1) RIPA powerful lysis buffer (Beyotime, China); protease inhibitor CM (Amresco, USA); phosphatase inhibitor PI (Amresco, USA); BCA protein analysis kit (Beyotime, China); protein 4× Loading Buffer (Novizan, China); Marker standard protein China); (Novizan, PVDF membrane (Sigma, USA); tetramethylethylenediamine (TEMED) (Sigma, USA); 0×electrophoresis solution pre-made powder (Servicebio, Wuhan); 10× transfer membrane solution pre-made powder (Servicebio, Wuhan); 10×TBST pre-made powder (Servicebio, Wuhan); sodium chloride (NaCl) (Sinopharm Group, China); isopropyl alcohol (Sinopharm Group, China); ammonium persulfate (AP) (Sigma, USA); glycine (Sinopharm Group, China) China); sodium dodecyl sulfate (SDS) (Sinopharm Group, China); Tris (Sinopharm Group, China); methanol (Sinopharm Group, China); skim milk powder (Yili Dairy, China); ultra-sensitive ECL chemiluminescence kit (NCM Biotech, China); 30% polyacrylamide solution (Servicebio, China); Tween (Sinopharm Group, China); mouse anti-human GAPDH antibody (Proteintech, China); rabbit anti-human TMED8 antibody (Invitrogen, USA); rabbit anti-human ERK1/2 antibody (CST, USA); rabbit anti-human ERK phosphorylated antibody (CST, USA); rabbit anti-human P38 antibody (CST, USA); rabbit anti-human P38 phosphorylated antibody (CST, USA); rabbit anti-human JNK antibody (CST, USA); rabbit anti-human JNK phosphorylated antibody (CST, USA); rabbit anti-human Casepase3 Antibodies (Santa, Japan); rabbit anti-human CD63 antibody (Abcam, USA); Rabbit anti-human CD81 antibody (Abcam, USA); rabbit anti-human CD9 antibody (Abcam, USA); mouse anti-human Ki-67 antibody (Wuhan Sanying, China); HRP-labeled goat anti-rabbit IgG antibody (Invitrogen, USA); HRP-labeled goat anti-mouse IgG antibody (Invitrogen, USA); CCK-8 kit (Beyotime, China); cell cycle analysis kit (Formax Biotech, China); cell apoptosis detection kit: AnnexinV-PE/7-AAD double-staining (KGI Biotech, China); and crystal violet staining solution (Beyotime, China).

2. The main instruments in the examples of the present disclosure include the following:

tissue chip system (UT06, Unitma, South Korea); inverted microscope (Leica, Germany); chemiluminescent gel imaging system (Bio-Rad, USA); fully automatic microplate reader (Bio-Rad, USA); electrophoresis system (Bio-Rad, USA); and cell culture incubator (Thermo Fisher, USA).

Example 1

Between 2020 and 2023, 79 formalin-fixed paraffin-embedded (FFPE) pancreatic cancer tissue samples, including cancer and tissues adjacent to cancer, were obtained from the Clinical Biobank of Affiliated Hospital of Nantong University. No cancer patients received any treatment, including radiotherapy, chemotherapy, or immunotherapy, and clinical case data were detailed and complete. This study protocol was approved by the Human Research Ethics Committee of Affiliated Hospital of Nantong University, China.

1. Production of Tissue Chips (1) According to the microscopic observation results of HE sections, the representative cancer nest areas in the wax block were marked.

(2) The paraffin wax and beeswax were mixed at a ratio of 1:1 to form a TMA blank receptor wax block. A 10×7-dot tissue array was designed on the wax block, and then holes were punched with a tissue chip instrument to make a TMA blank wax block.

(3) The most representative cancer nest area was selected at the marked point on the donor wax block, and a tissue block with a diameter of 2 mm was collected, with 1 core from each case.

(4) The tissue cores were transferred to the holes of the recipient wax block, with a certain distance between each tissue core, and the corresponding tissues adjacent to cancer were selected as a control.

(5) The tissue array block was fused by heating in a 55° C. incubator for 10 min, the wax block was taken out before it was about to melt, and allowed to cool to room temperature, such that the receptor wax block and the donor tissue were integrated.

(6) Before slicing, the tissue chip was pre-cooled at 4° C. for about 4 h, and then the tissue array block was corrected with a fully automatic tissue slicer at 20 mm/revolution until all tissues were complete.

(7) The tissue array block was sliced with a microtome, obtained continuous slices were floated in cold water to allow them to unfold naturally, and then the slices were transferred to warm water at 45° C. to unfold for about 2 min. After unfolding, the slices were spread on a slide that had been treated to prevent detachment and allowed to air-dry.

(8) The slices were baked in a high-temperature oven at 60° C. for 3 min, and then baked at 58° C. for 18 h.

(9) The prepared tissue chips were stored in a sectioning box at −20° C. for later use.

2. Immunohistochemistry (1) The tissue chip was baked in a constant-temperature oven at 60° C. for about 40 min until the paraffin was melted.

(2) The chip was soaked in xylene I, xylene II, 100% ethanol I, and 100% ethanol II for 5 min each, and then soaked in 95% ethanol, 90% ethanol, 80% ethanol, and 70% ethanol for 2 min each, and then rinsed with water.

(3) An antigen retrieval solution was placed in an immunohistochemistry box in advance, preheated to 95° C. using a water bath, then the chip was placed in the box to allow treatment at 95° C. for 20 min for antigen retrieval, naturally cooled to room temperature, and then rinsed with PBS 3 times, 5 min each time.

(4) A boundary line was drawn with an immunohistochemistry pen to obtain a circle around the tissues on the chip, the inside of the circle was filled with 3% $H_2O_2$, and the tissues were incubated for 10 min, and then washed 3 times with PBS for 5 min each time.

(5) A primary antibody (rabbit anti-human TMED8 antibody) was added dropwise and incubated overnight at 4° C.

(6) Rewarming was conducted at room temperature for 1 h to remove the primary antibody, the tissues were rinsed with PBS 3 times for 5 min each time, a polymer enhancer was added dropwise, and incubated at room temperature for 20 min; and the tissues were washed with PBS 3 times for 5 min each time.

(7) A secondary antibody (enzyme-labeled anti-mouse/rabbit IgG polymer) was added dropwise, incubated at room temperature for 30 min, and then wash with PBS 3 times for 5 min each time.

(8) A freshly prepared DAB reagent was added dropwise, and after color development, the chip was rinsed with tap water for 5 min to terminate the color development.

(9) The chip was subjected to hematoxylin staining for 2 min, and immediately rinsed slowly with running water, then soaked in 0.5% HCl ethanol solution for 2 min, and rinsed with running water for 15 min.

(10) The chip was soaked in 80% ethanol, 90% ethanol, 95% ethanol, 100% ethanol I, 100% ethanol II, and xylene for 1 min each, and air-dried naturally in a fume hood.

(11) The tissue was sealed with neutral gum.

3. Determination of Results

According to a degree of staining of cells in the tissues, the positive intensity was divided into 3 levels. No positive coloring was grade 0 (negative), light yellow was grade 1 (weak positive), brown was grade 2 (moderate positive), and tan was grade 3 (strong positive). Cell positivity rate=number of positive cells/total number of cells, which was divided into 4 levels; the rates of levels 0 to 4 are 0% to 5%, 6% to 25%, 26% to 50%, 51% to 75%, and >75%. The chip results were scored by 3 pathologists based on independent readings and then divided into four groups according to the quartiles of the scores: "−, +, ++, and +++" for statistics and analysis.

The results of immunohistochemical staining of 79 cases of pancreatic cancer tumors and slices for tissues adjacent to cancer were shown in FIG. 1. The positive TMED8 protein was mainly expressed in the cytoplasm of tumor cells and the interstitium of cancer tissues in brown-yellow color, while showing low expression or no expression in most tissues adjacent to cancer. Statistical results showed that the TMED8 gene was indeed highly expressed in pancreatic cancer tissue chips *$P<0.05$.

Figure 2:
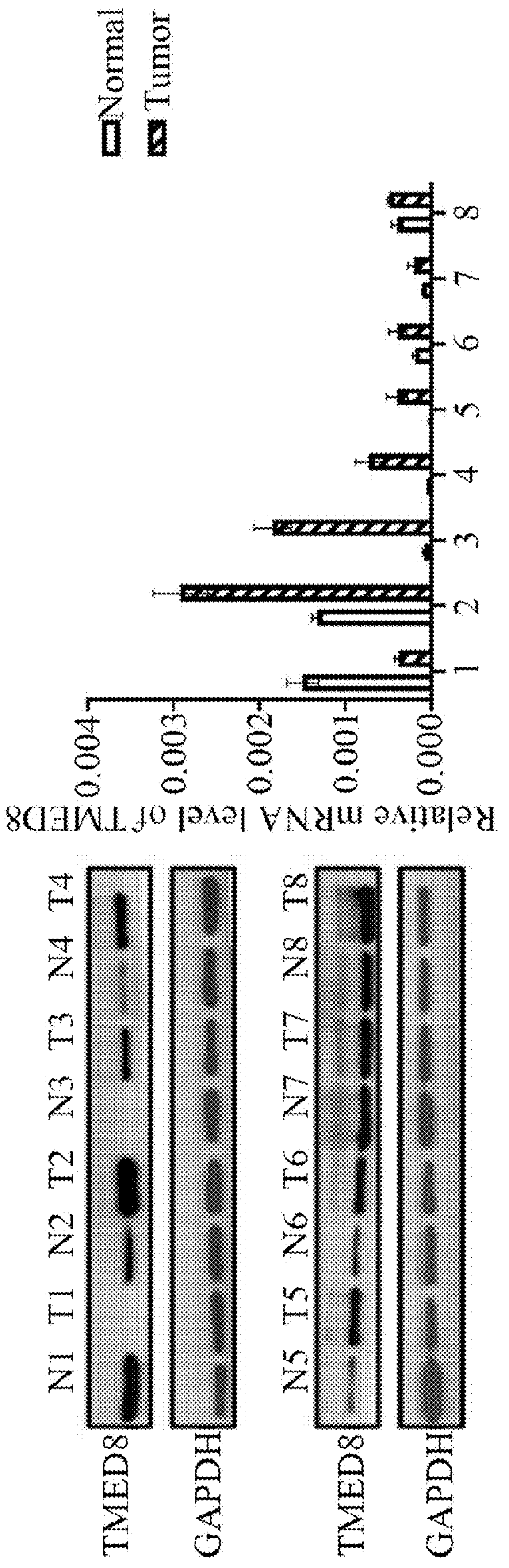
FIG. 2 shows the expression of TMED8 gene and the corresponding WB and PCR verification results.
Figure 3:
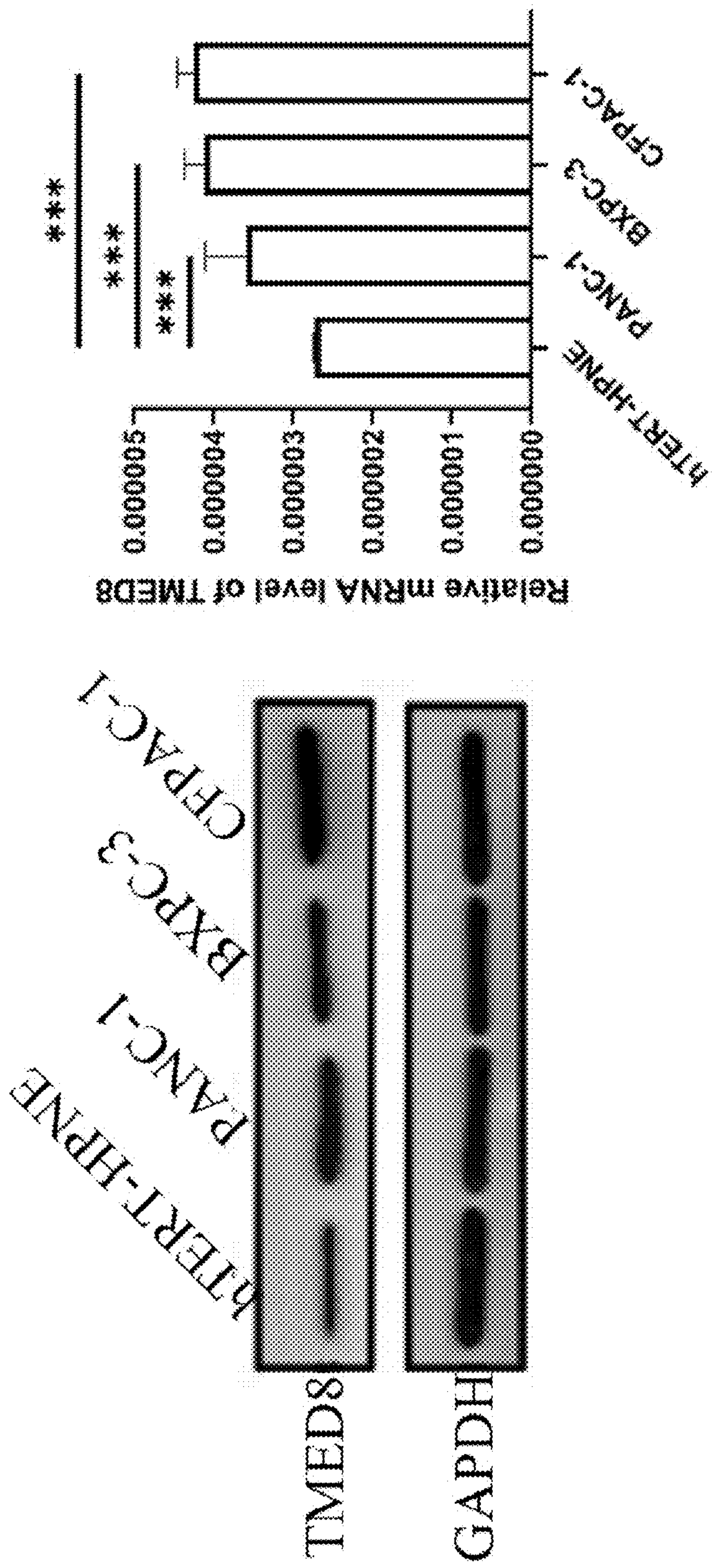
FIG. 3 shows a comparison of the expression of TMED8 gene in normal ductal epithelial cells and tumor cell lines of pancreatic cancer.

8 pairs of cancer tissues and tissues adjacent to cancer from pancreatic cancer patients were selected for WB verification. The results were shown in FIG. 2, and consistent with the above data.

Example 2

1. Cell Transfection (1) Transformation and extraction of plasmid: a dry powder of an overexpression plasmid pLV3-CMV-TMED8 (human)-3×FLAG-EF1a-CopGFP-Puro of the TMED8 gene stored in a −20° C. refrigerator was dissolved with 40 μL of DEPC water. An electric thermostatic water bath was heated to 42° C., while DH5a competent cells stored in a −80° C. ultra-low temperature refrigerator were thawed on ice; when the competent cells were completely thawed, the transformation experiment was started immediately.

Figure 10:
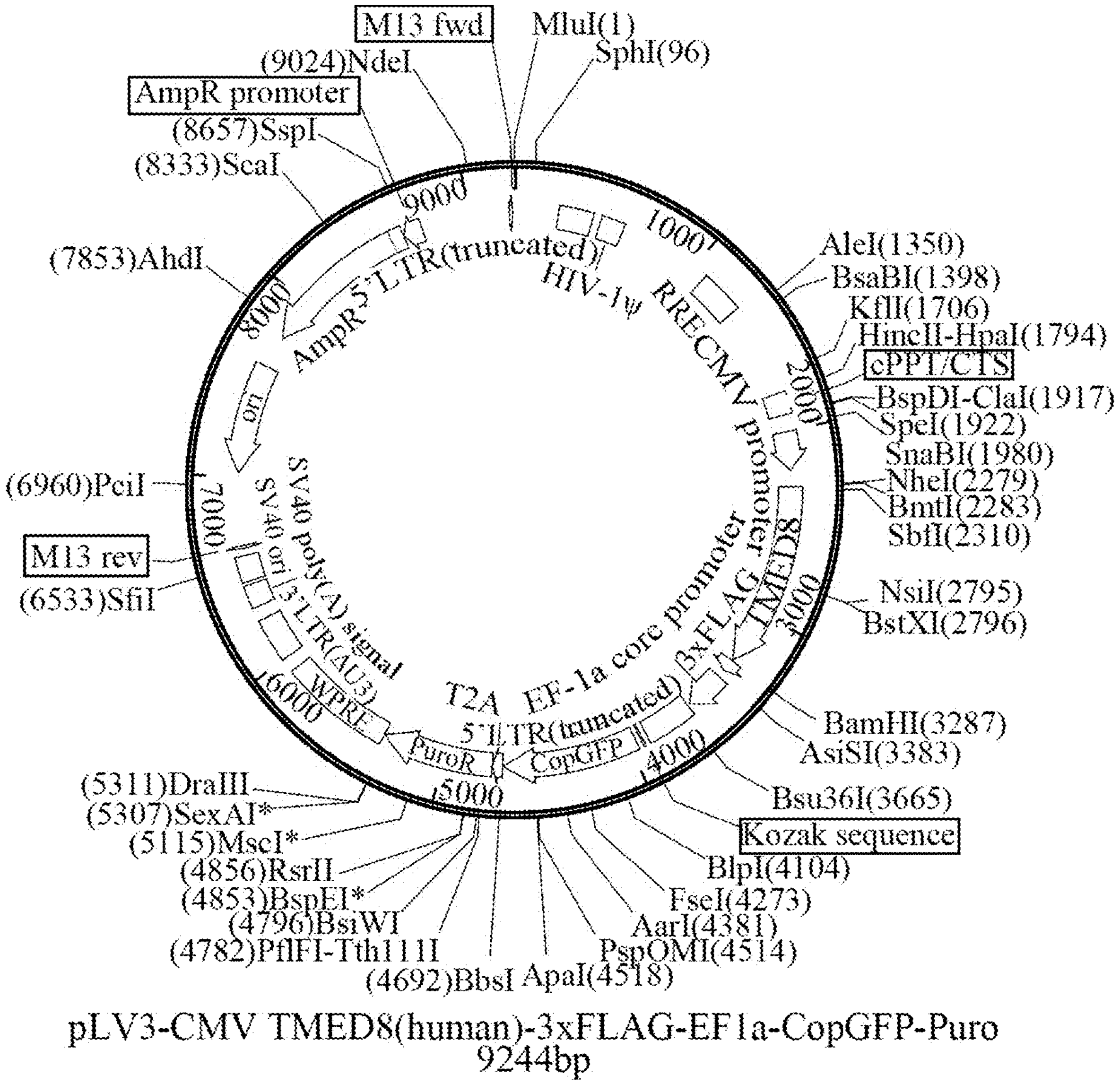
FIG. 10 shows a construction map of an overexpression plasmid pLV3-CMV-TMED8 (human)-3×FLAG-EF1a-CopGFP-Puro of the TMED8 gene.

The overexpression plasmid of the TMED8 gene (FIG. 10) was mixed with the thawed competent cells at a volume ratio of 1:3, mixed well by flicking the tube wall and blowing gently 2 to 3 times; a resulting mixture was allowed to stand on ice for 25 min, incubated in a 42° C. water bath for exactly 45 s, and immediately transferred to ice for 3 min; a resulting transformed plasmid was transferred to a shaking tube containing 40 μL of antibiotic-free LB liquid medium to allow pre-shaking in a constant-temperature shaker at 37° C. and 200 rpm for 1 h; 4 mL of a liquid medium containing ampicillin at a concentration of 50 μg/mL was added, and the bacterial cells were shaken at 250 rpm and 37° C. overnight for 14 h to 16 h to avoid the growth of miscellaneous bacteria; a resulting bacterial solution was extracted using the Axygen plasmid extraction kit according to a standard procedure, and an obtained plasmid concentration was measured and recorded; the remaining bacterial solution could be mixed with glycerol to allow preservation and then stored at −80° C.

Figure 4:
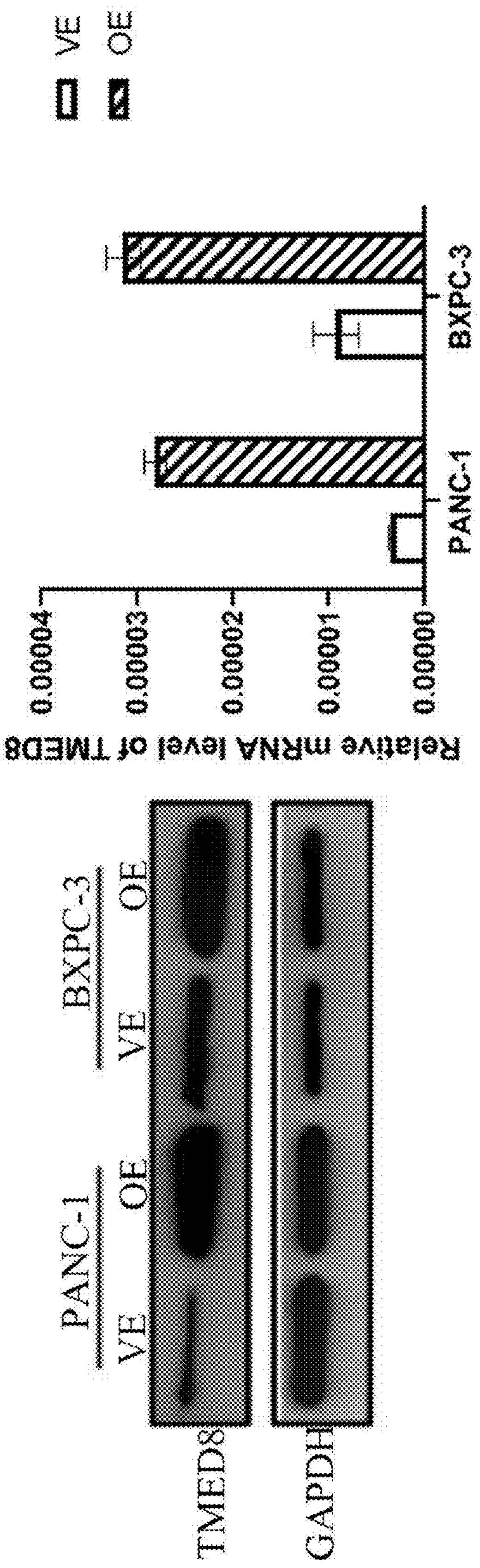
FIG. 4 shows verification for the efficiency of TMED8 gene overexpression in stably-transfected cell lines of pancreatic cancer.

(2) Establishment of stably-transfected cell lines: an appropriate amount of wild-type cells to be transfected (PANC-1 and BXPC-3 pancreatic cancer cell lines) were inoculated in a 6-well plate, until a cell density reached 60% to 70% after 6 h of adherence; 80 μL of 1640 basal medium without serum and double antibodies were fused with 3 μg of the plasmid, mixed well by flicking the tube wall without pipetting with a pipette to avoid DNA breakage, and allowed to stand at room temperature for 5 min; 3 μL of Lipofectamine 2000 transfection reagent was added, allowed to stand at room temperature for 20 min to 30 min, added into a complete medium of the 6-well plate, mixed well by gently pipetting with a pipette, and incubated in a cell incubator at 37° C. and 5% carbon dioxide for 24 h to 48 h; the cell state was observed once in the first 24 h, and then observed once every 12 h, where once the cell status deteriorated due to the toxicity of the transfection reagent, the medium was changed immediately; after the transfection was stable, a cell transfection efficiency was observed using fluorescent tag of the plasmid under a fluorescence microscope; after the transfection was successful, the wild-type cells that had not been successfully transfected were screened with corresponding resistance, usually puromycin, and the successfully-transfected cells were selected to establish a stably transfected cell line; after passage and preservation, a total cell protein or total RNA was collected for WB or qRT-PCR to verify the overexpression efficiency of the cells. The results were shown in FIG. 4.

2. CCK-8 Cell Proliferation Activity Detection

The over-expressed stably transduced cells and wild-type control cell lines to be tested were separately pre-cultured in a medium dish, when the confluence of the cells in the dish reached 90%, the cells were digested and resuspended. It was noted that the amount of cells in the dish must be properly controlled since cells growing in a crowded state might trigger their own apoptosis, affecting the accuracy of subsequent results. The cells were counted and inoculated in a 96-well plate at 5,000 to 10,000 cells per well according to the cell growth characteristics. Each group was set with 5 to 6 replicate wells to reduce experimental errors caused by operating techniques. It was noted that the number of cells in the control group and the treatment group must be equal to achieve controlling variables. Detection of cell proliferation activity began 6 h to 12 h after the cells adhered to the wall. Since cell proliferation activity needed to be continuously tested for 5 d based on the cell doubling cycle, experimental operations and result testing should be conducted at a same time point every day.

A CCK8 reagent was mixed with a basal medium of the corresponding cells at a volume ratio of 1:9 to obtain a fresh working solution. The medium in the original well was discarded. After washing with 1×PBS buffer, 100 μL of 10% CCK8 working solution was added to each well and allowed to stand for 1 h to 2 h in a 37° C. incubator, and an absorbance at 460 nm was measured using a microplate reader. The data were recorded, and data processing and comparative analysis were conducted after all tests were completed.

Figure 6A:
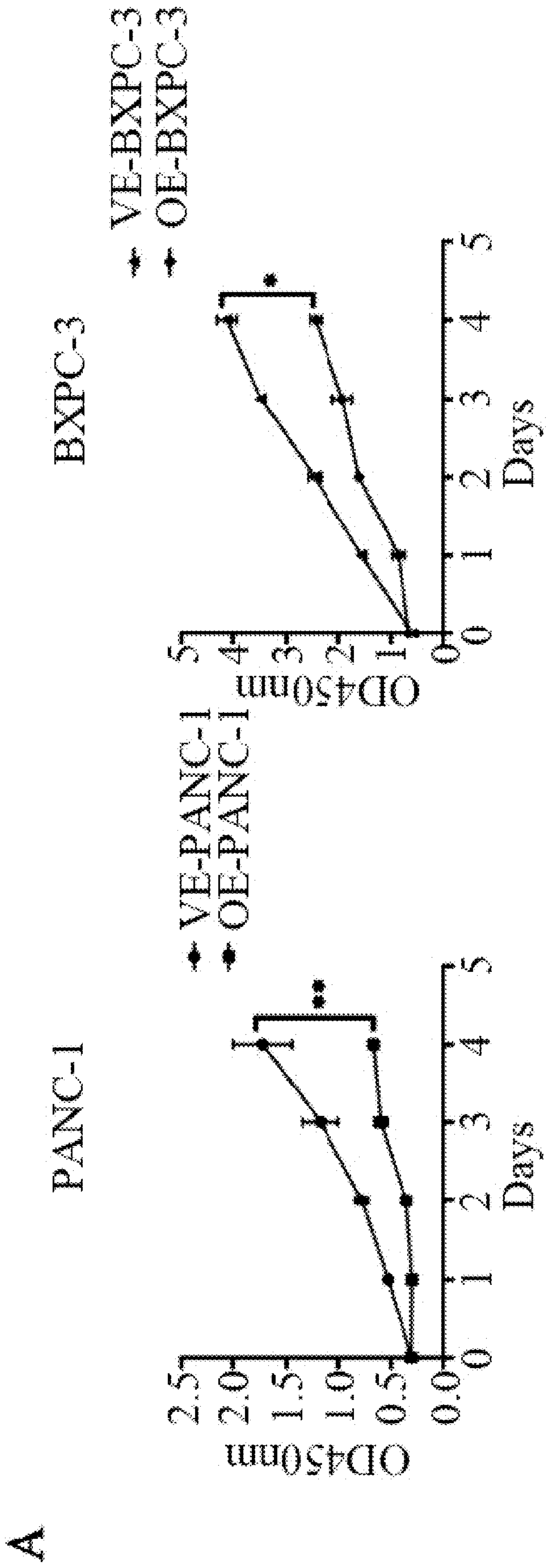
FIGS. 6A-C show an influence of overexpression of the TMED8 gene on a proliferation ability of pancreatic cancer cells studied by CCK8 and colony formation experiments.
Figure 6B:
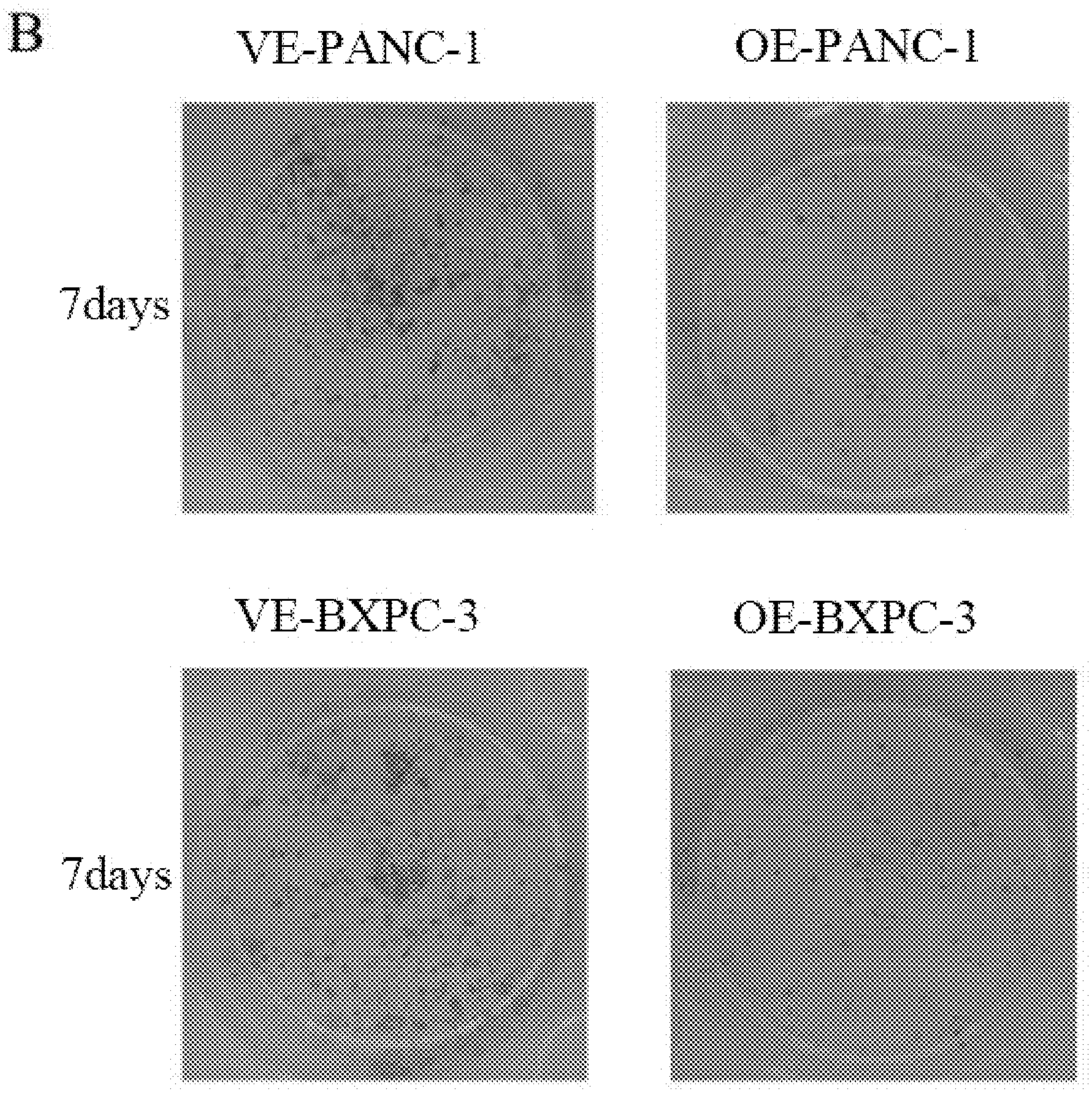
Figure 6C:
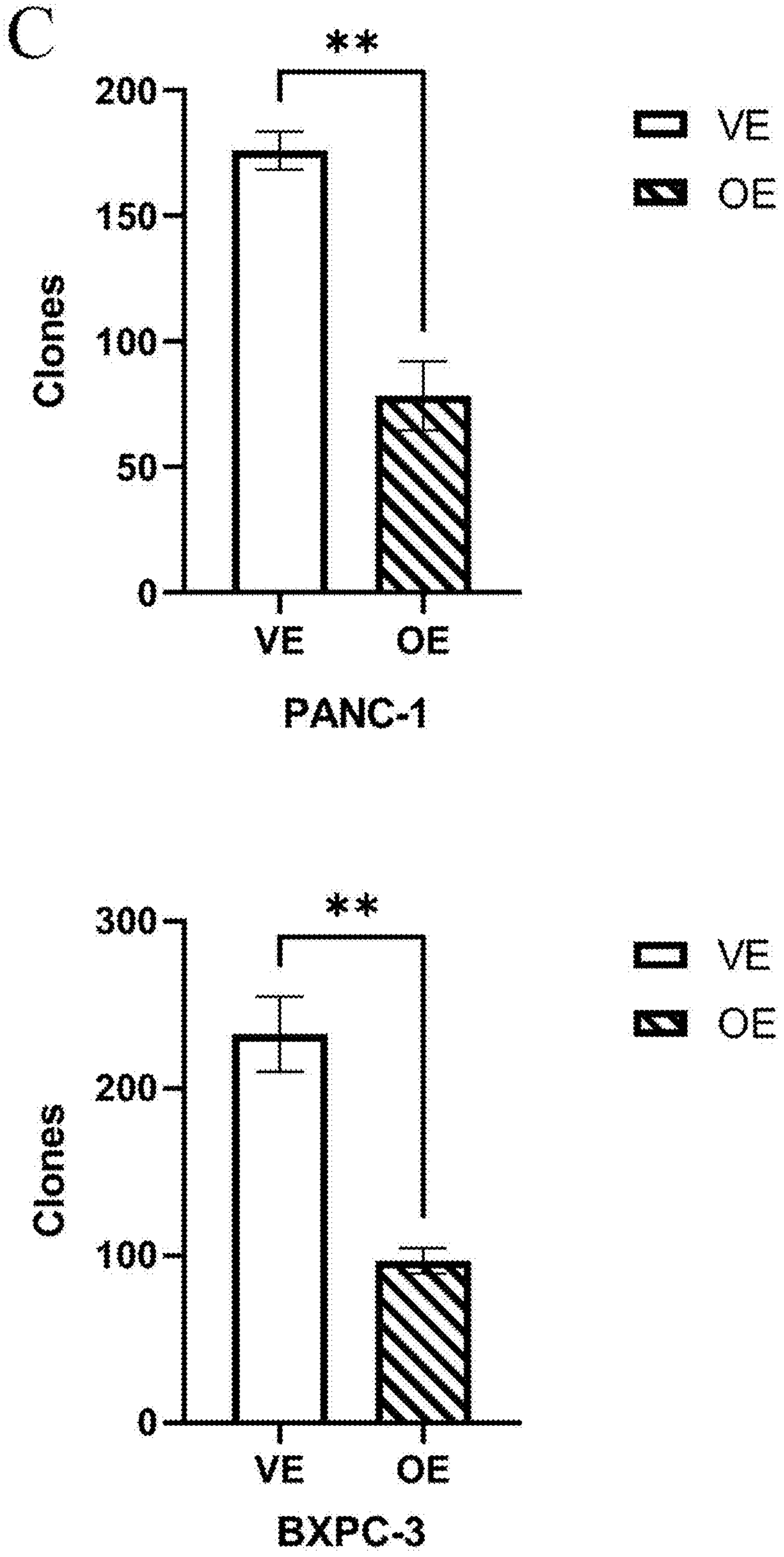

The results were shown in FIG. 6. Overexpression of the TMED8 gene inhibited the proliferation of pancreatic cancer cells.

3. Cell Scratching Healing Experiment

A brand new sterile packaged six-well plate was placed upside down on a clean workbench, a nine-square grid coordinate line was drawn on the bottom of the well plate using a ruler and a marker, so as to facilitate positioning for photos taken under a microscope for later scratch experiments. Appropriate amounts of wild-type and overexpression cell lines were inoculated in a six-well plate, with 3 replicate wells in each of the control group and overexpression group. According to the growth cycle, the cells were cultured with fresh complete nutrient medium to 90% density, and cell scratching was conducted with an alcohol-sterilized ruler and a 1 mL sterile blue pipette tip. During the cell scratching, it was noted that verticality and uniform strength were required, the size of the scratches in each repeated hole should be controlled to be basically equal to reduce the result error caused by the operation and to better control the experimental variables. 3 scratch lines were also drawn in each well to ensure the repeatability of experimental results. After cell scratching was completed, 1×PBS buffer was added to clean the floating cells and cell debris with gentle force to prevent cells from being washed away at the scratch boundary. The complete medium with low serum concentration was replaced to maintain cell growth while controlling the growth rate for subsequent observation. A time point as 0 h from the start of the experiment was recorded, and photos were taken every 24 h. The healing status of cell scratches were observed under a microscope and photos were taken, and the final results of the experiment were integrated and analyzed 72 h later.

Figure 5A:
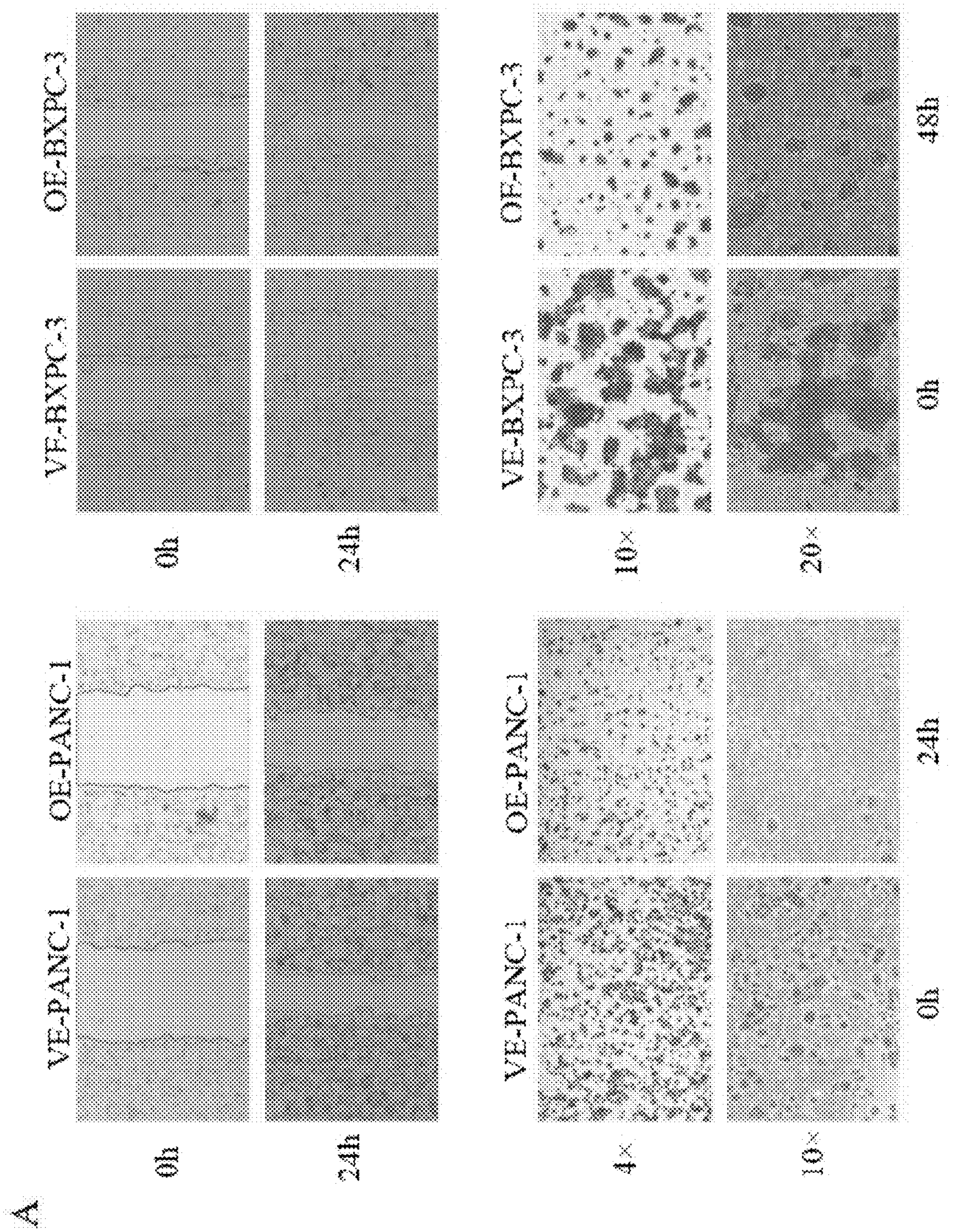
FIGS. 5A-B show an influence of overexpression of the TMED8 gene on a migration ability of pancreatic cancer cells studied by cell scratching and Transwell experiments.
Figure 5B:
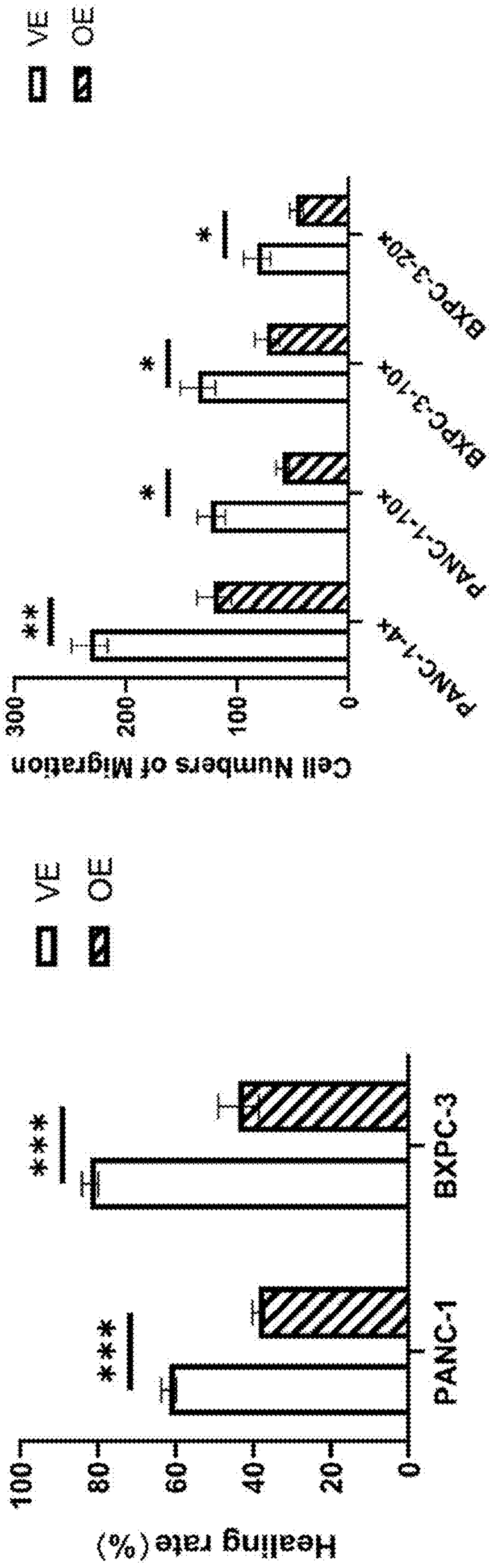

The results were shown in FIG. 5. Overexpression of the TMED8 gene inhibited the migration ability of pancreatic cancer cells.

4. Cell Colony Formation Experiment

The cells to be tested were digested into a single state using trypsin containing EDTA, the cell suspension was collected, and the cells were counted. According to the number of 500 cells per well, the cells in the control group and the overexpression group were inoculated in 6-well plates, each group had 3 replicate wells. 2 mL of freshly cultured cells were added to each well and placed in a cell culture incubator, cultured at 37° C. and 5% carbon dioxide for 5 d to 7 d. Since the initial number of cells was low, there was no need to change the medium during colony formation. After 5 d to 7 d, the culture plate was taken out to observe the colony formation status under a microscope. After washing with 1×PBS, 1 mL of 4% paraformaldehyde fixative was added to each well to fixate for 2 h, washed 3 times with PBS, and then stained with crystal violet dye for 1 h. The working solution was discarded, the cells were rinsed with double-distilled water and dried, and then photos were taken to observe the difference in colony formation between the two groups of cells.

The results were shown in FIG. 6. Overexpression of TMED8 gene inhibited the formation of pancreatic cancer cell colonies, that is, inhibited the proliferation ability of pancreatic cancer cells.

5. Transwell Cell Migration Experiment

The cells to be tested were digested, resuspended, counted, and set aside for later use. A 24-well cell culture plate and the matching chamber with an 8 μm transparent PET film were taken, the chamber was placed in the culture well of the 24-well plate, and 600 μL of complete nutrient medium containing 5% fetal bovine serum was added outside the chamber slot or into the culture hole. 30,000 cells were counted and aspirated, fully resuspended in 200 μL of basal nutrient medium without fetal bovine serum, transferred with a pipette to the chamber, and cultured for 24 h to 72 h according to the cell growth cycle to allow the cells to fully penetrate the biofilm, and the migration ability of the cells was observed. The chamber was taken out, the medium inside was discarded, and the chamber was placed in a clean 24-well plate, soaked in 4% paraformaldehyde fixative for 2 h, rinsed gently with double-distilled water, and then stained with crystal violet staining solution for 1 h. The cells were washed with double-distilled water after staining. If the staining was excessively and affected the observation of the results, methanol was added to allow decolorization and rinsing to elute the crystal violet in the blank areas of the membrane. After the staining was completed, the chamber was placed upside down, dried at room temperature, observed with an ordinary optical microscope, and photos were taken at a suitable field of view.

The results were shown in FIG. 5. Overexpression of the TMED8 gene inhibited the migration ability of pancreatic cancer cells.

6. Flow Cytometry

Flow cytometry of cell apoptosis: PE fluorescein-labeled Annexin V dye and 7-AAD dye were added to double-stain the cells to be tested to detect cell apoptosis. First, the cells were digested and collected with EDTA-free trypsin, washed 2 to 3 times with 1×PBS cell washing solution, and counted. Each sample was generally controlled at 10,000 to 50,000 cells, without fixation to prevent subsequent quenching of fluorescence. The collected clean cell pellet was resuspended in 100 μL buffer, 1 μL of Annexin V dye and 5 μL 7-AAD dye were added to each 100 μL of suspension, mixed gently and stored in the dark at room temperature to allow staining at room temperature, reacted for 5 min to 10 min, then added with 400 μL of buffer, mixed well, transferred to a flow cytometer professional test tube, and the on-machine detection was completed within 1 h. PE was orange-red fluorescence, with an excitation wavelength of Ex=488 nm and an emission wavelength of Em=578 nm, and FL2 channel was recommended. 7-AAD dye was red fluorescent with an excitation wavelength of Ex=546 nm and an emission wavelength of Em=647 nm, and FL3 channel was recommended. Fluorescence compensation and adjustment were required during subsequent data analysis.

Figure 7A:
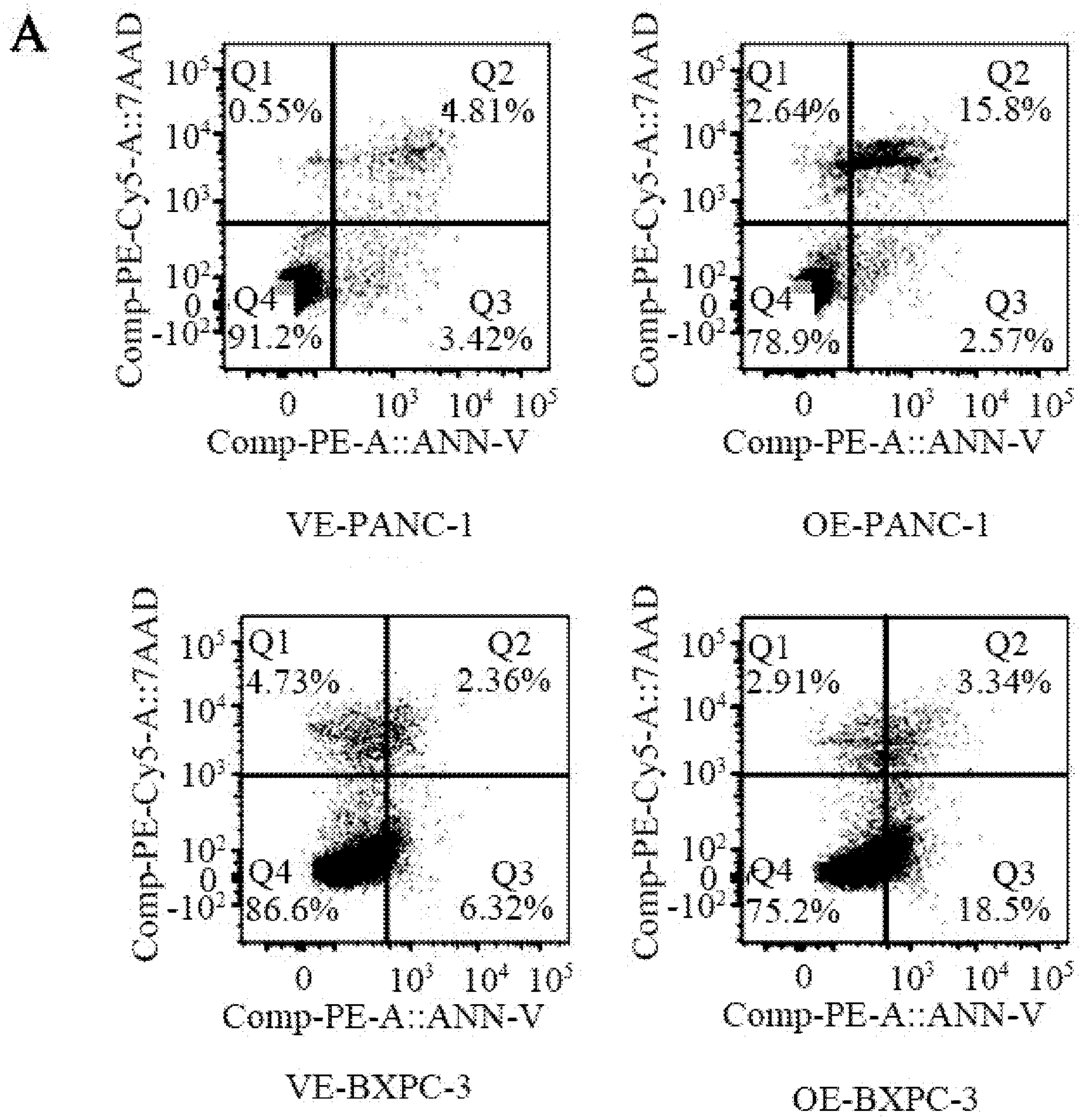
FIGS. 7A-B show an influence of overexpression of the TMED8 gene on an apoptotic ability of pancreatic cancer cells detected by flow cytometry.
Figure 7B:
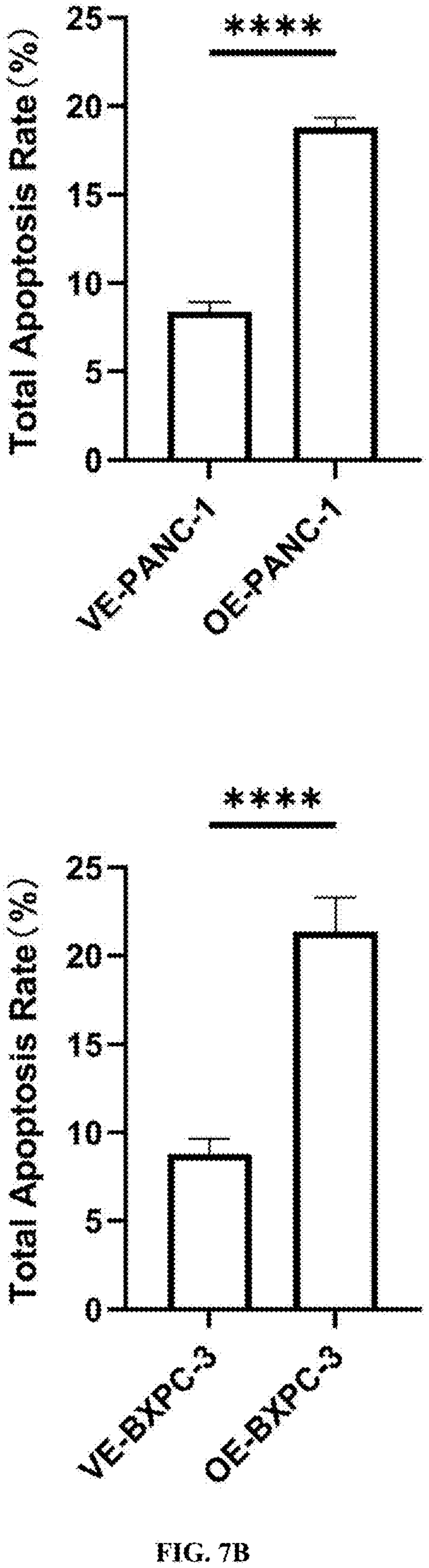
Figure 8A:
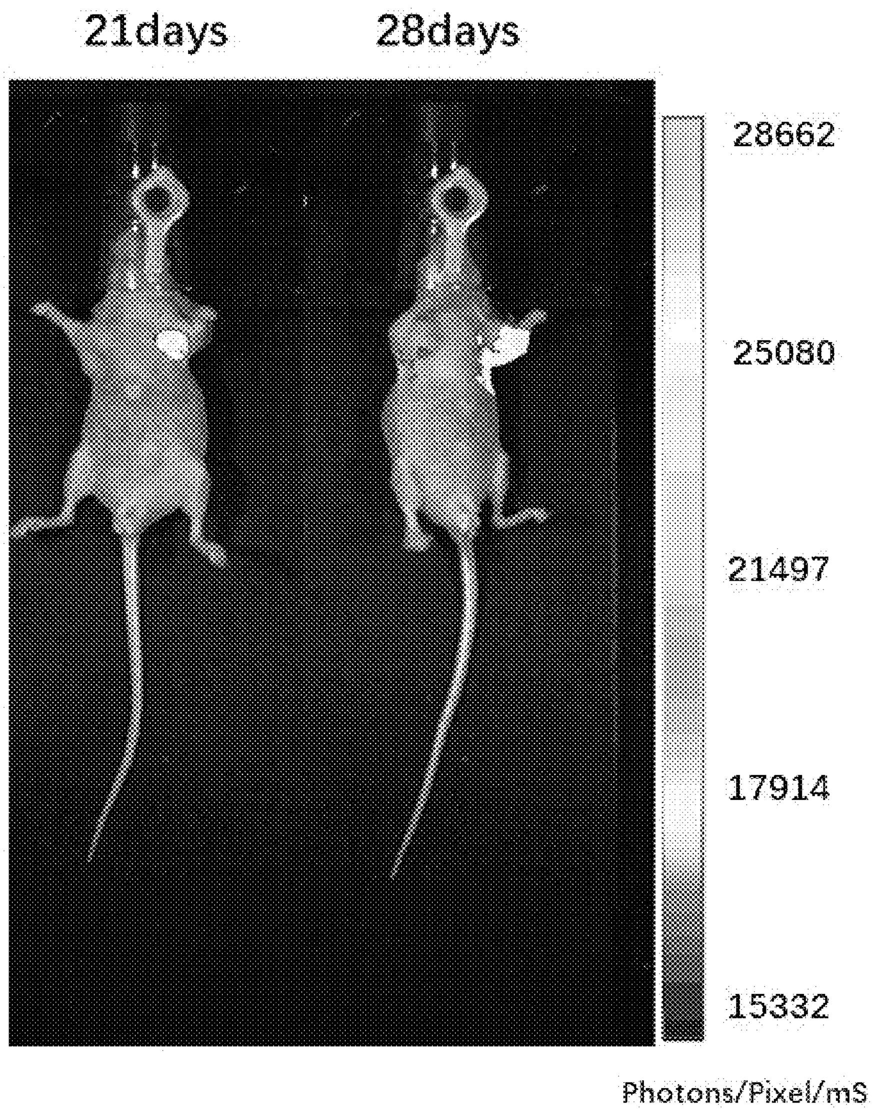
FIGS. 8A-E show an influence of overexpression of the TMED8 gene on subcutaneous tumor formation of pancreatic cancer cells in nude mice.
Figure 8B:
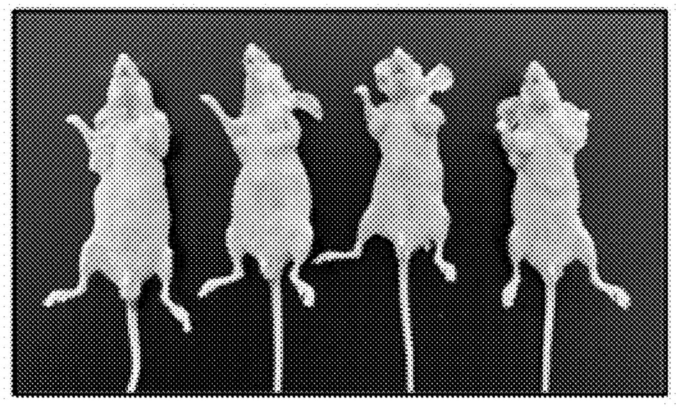
Figure 8C:
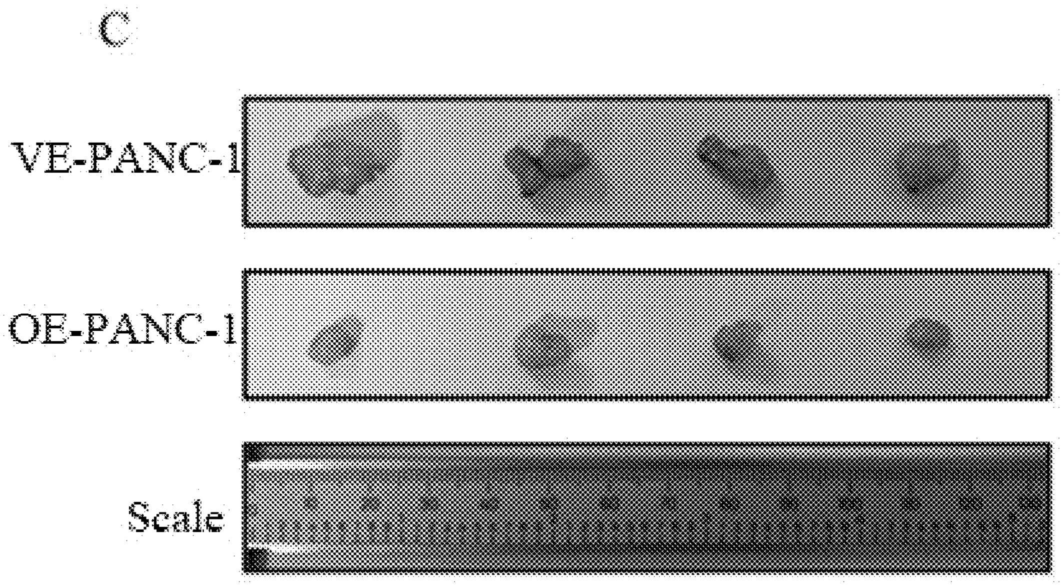
Figure 8D:
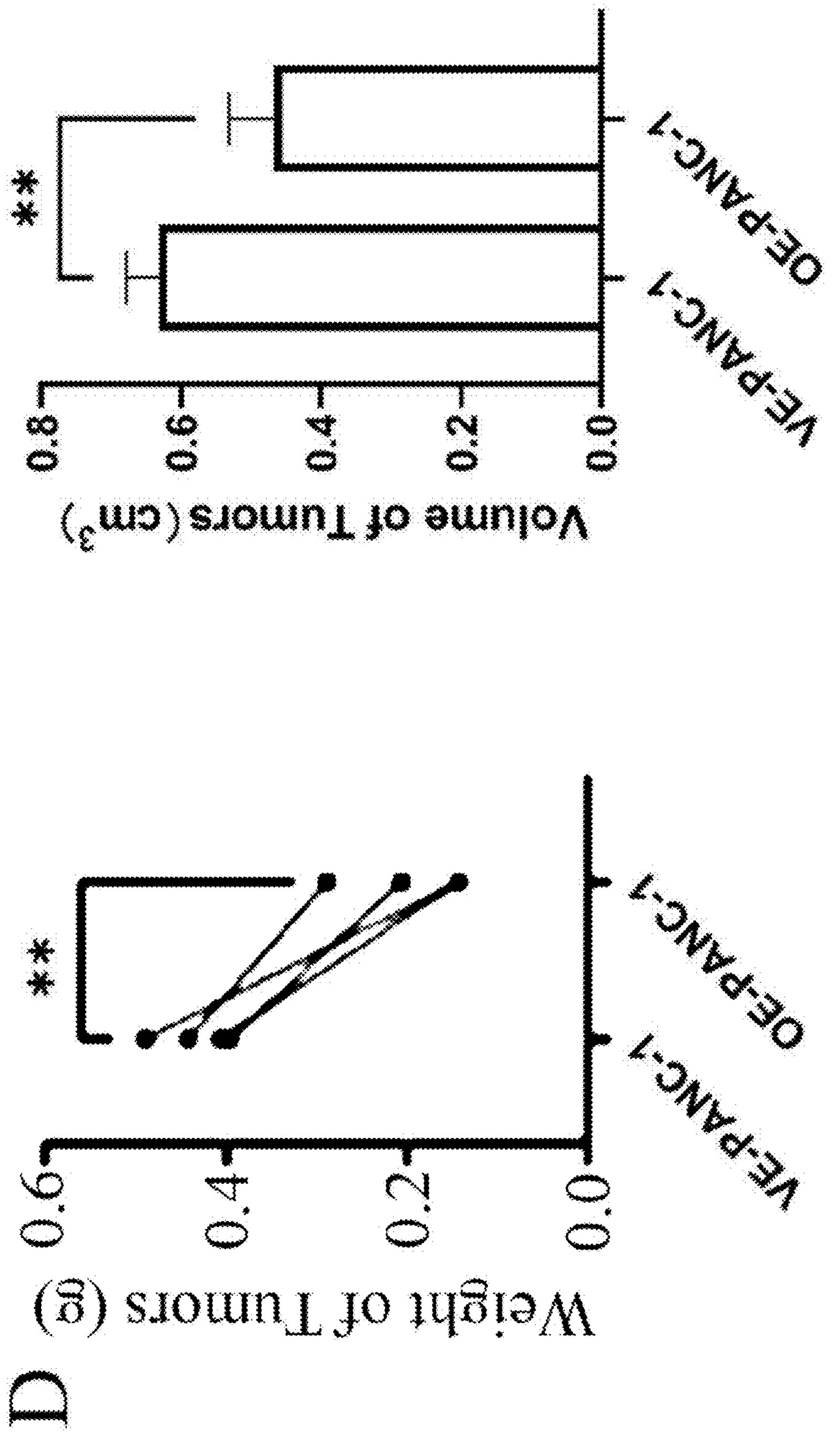
Figure 8E:
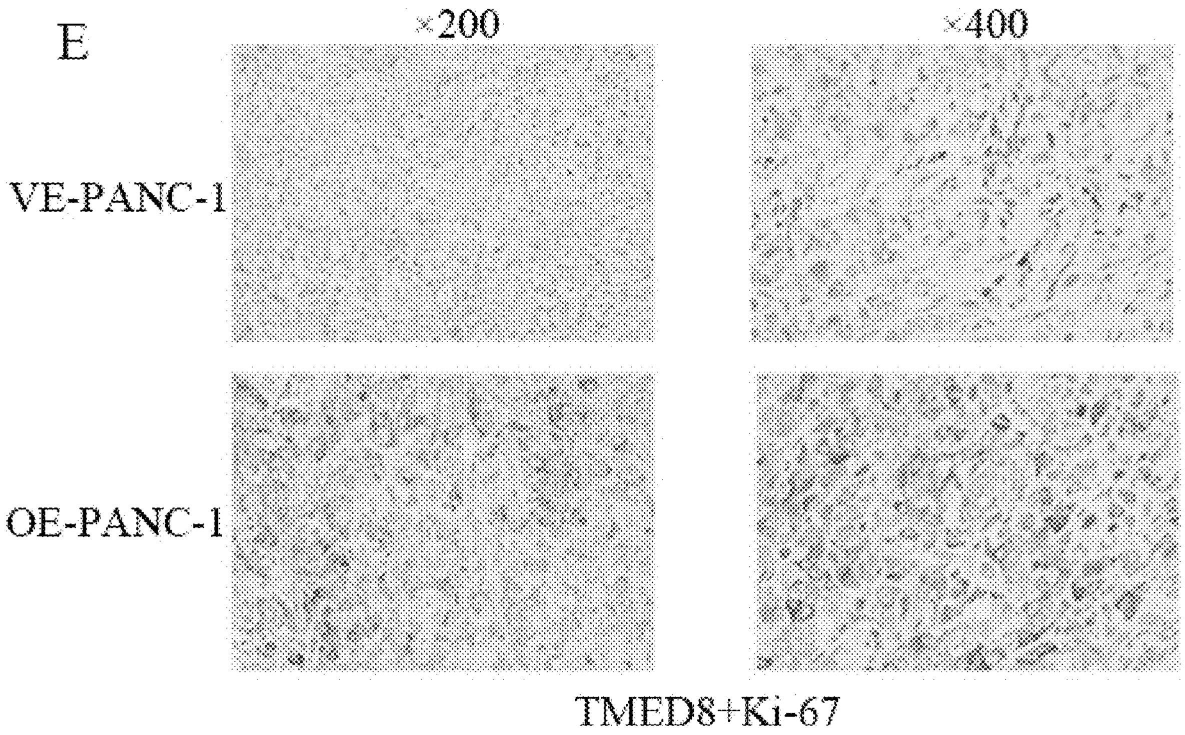
Figure 9A:
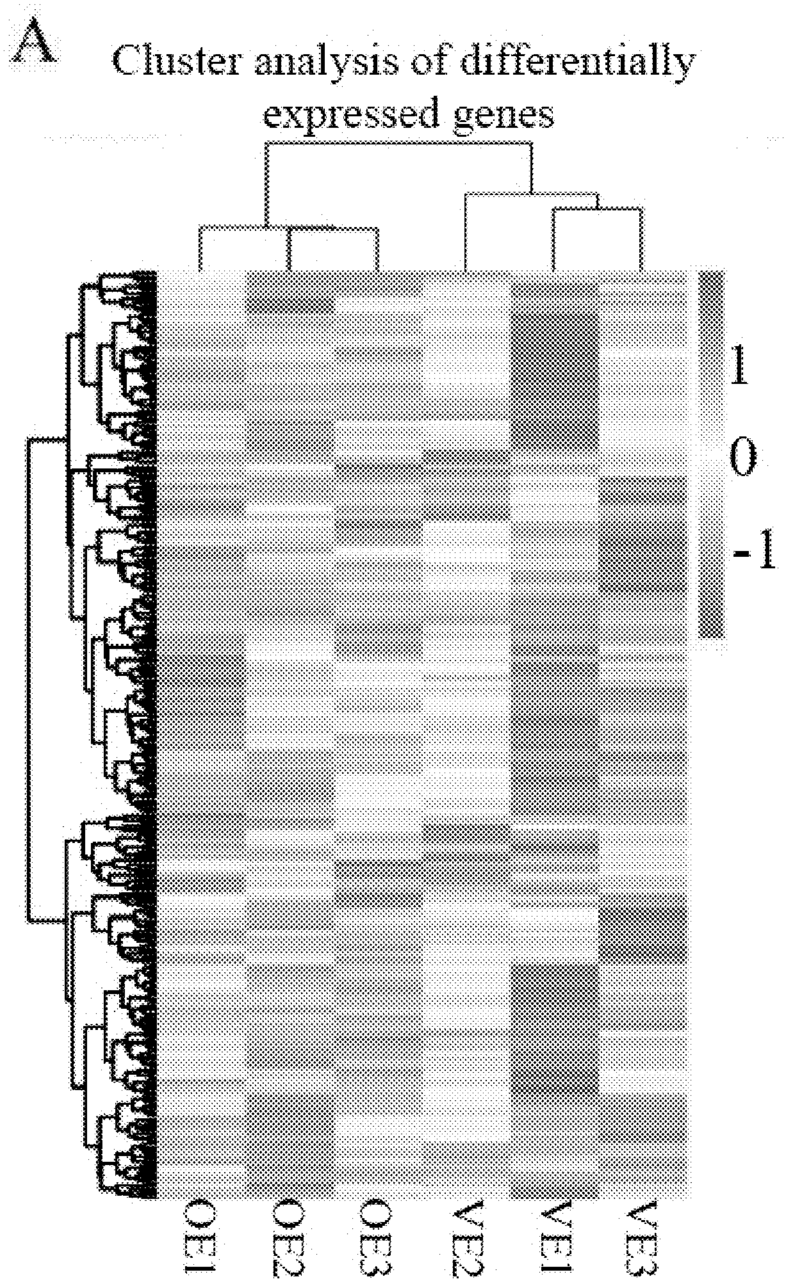
FIGS. 9A-D show an influence of increasing TMED8 gene expression on MAPK-related molecules.
Figure 9B:
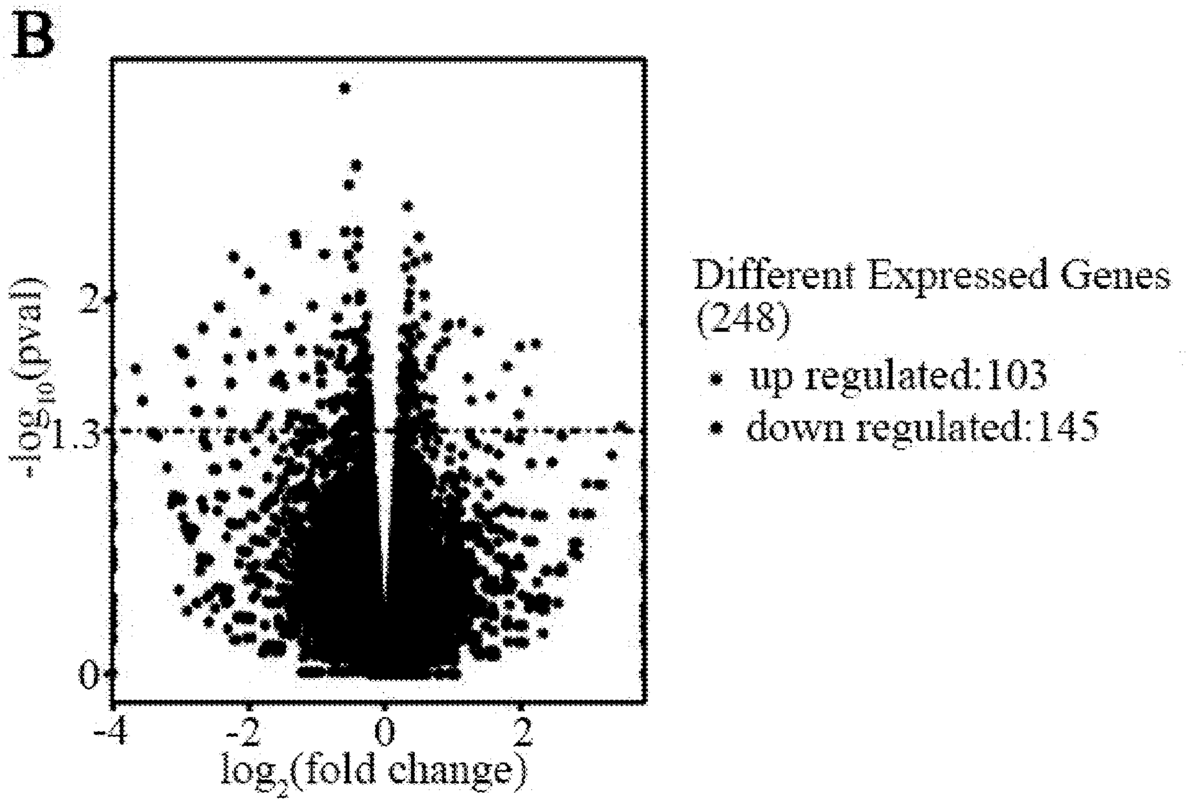
Figure 9C:
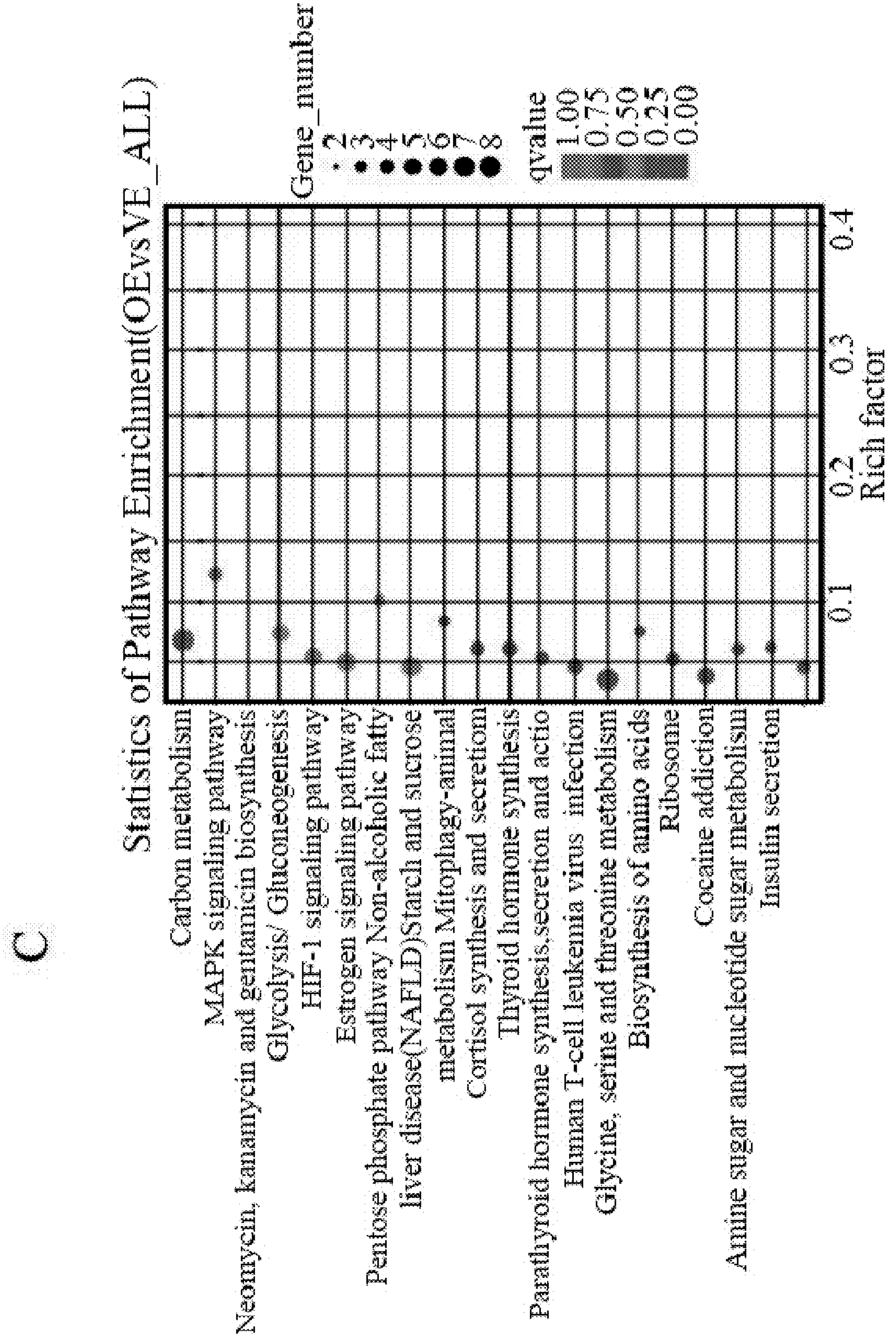
Figure 9D:
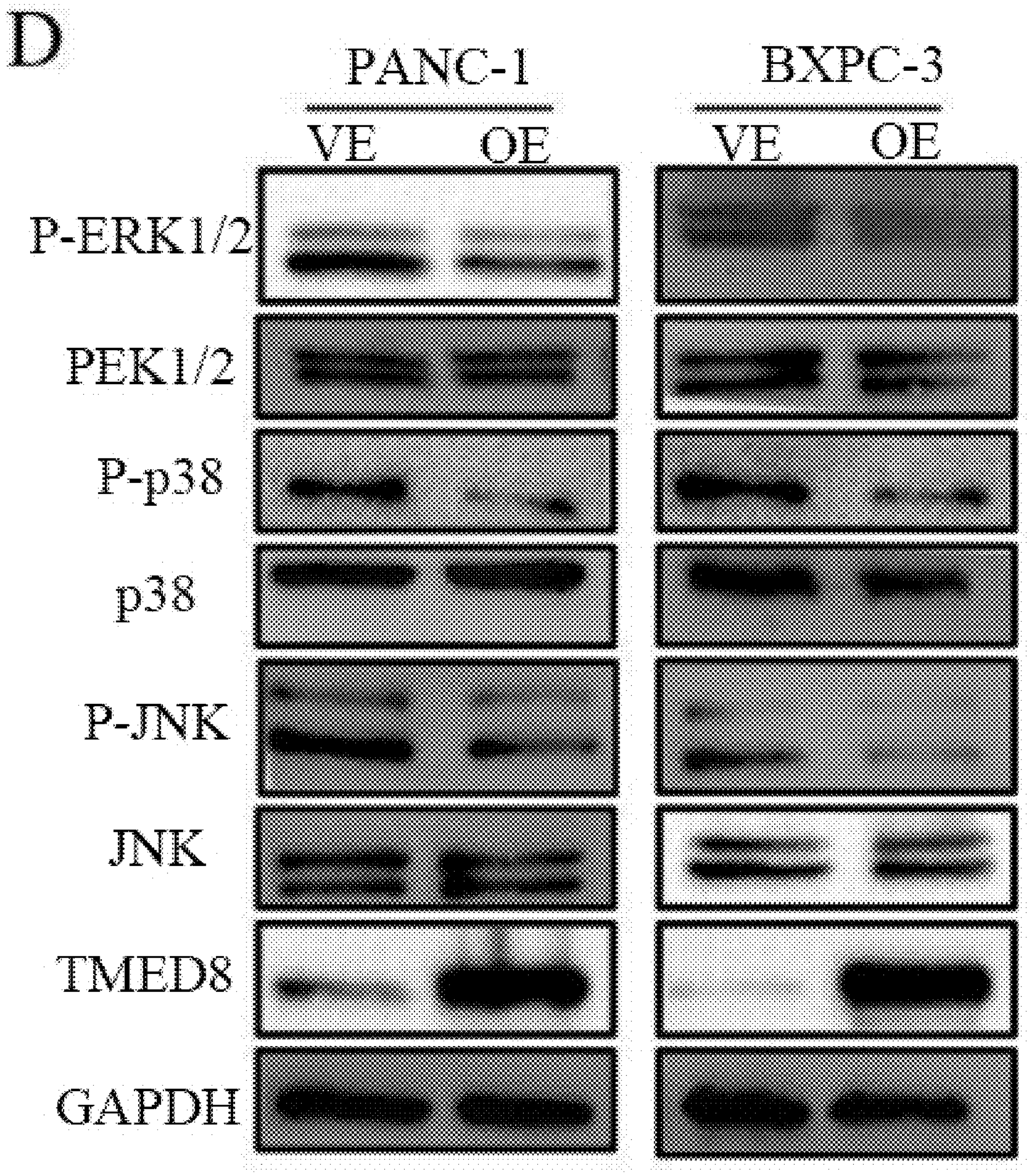

The results were shown in FIG. 7. Overexpression of TMED8 gene promoted apoptosis of pancreatic cancer cells.

7. Subcutaneous Tumor Formation in Nude Mice 4-week-old male BALB/c immunodeficient nude mice were selected for subcutaneous tumor formation experiments. Before the experiment, each nude mouse was weighed and recorded, and the PANC-1 control cells and overexpressed cells were digested with trypsin and counted. It was appropriate to inject approximately $2\times10^7$ cells of each type into each nude mouse and resuspend in sterile 1×PBS solution. It was noted that the cell suspension must be placed on ice before animal experiments to avoid cell damage and death. Equal amounts of TMED8-overexpressing PANC-1 cells and PANC-1 control cells were injected into the left and right armpits of the upper limb of a same nude mouse. After that, the condition of the mice needed to be observed every day. After 4 to 6 weeks of tumor formation, the nude mice were sacrificed and dissected, tumors were removed, weighed and measured, and then fixated for subsequent immunohistochemistry experiments. It was noted that conducting control experiments on the same nude mouse facilitated the control of interfering factors caused by mouse heterogeneity, thus more intuitively determining the impact of TMED8 gene on tumor growth in vivo.

The results were shown in FIG. 8. The TMED8 gene inhibited the tumor-forming ability of pancreatic cancer cells under the skin of nude mice, that is, inhibited the proliferation of pancreatic cancer cells in the animal body.

8. Western Blot (1) Extraction of total protein from cells and tissues: during the entire process, the cell samples to collect total protein should be placed on ice, the medium in the dish was discarded, and the cells were washed with 1×PBS solution, and added with 0.2 mL to 0.4 mL of RIPA effective lysis solution. After about half an hour of lysis, the cells were scraped with a cell scraper, transferred to a 1.5 mL centrifuge tube, and placed in an electric rotator at 4° C. for rotation overnight to fully lyse the protein. The cells were centrifuged at 7,500 rpm for 15 min, the supernatant was collected to discard the cell debris, ¼ of the total volume of the supernatant sample buffer (Loading Buffer) was added, and boiled for at least 30 min to ensure that the protein was fully heated and denatured. After cooling to room temperature, the protein was aliquoted and stored in −20° C. or −80° C. refrigerator to avoid protein degradation due to repeated freezing and thawing.

(2) Preparation of SDS-PAGE gel: the gel plate was washed, dried, and clamped on a gel preparation rack, double-distilled water was added to check for leaks. After passing the leak check, the gel plate was dried vertically and the gels were prepared according to the component proportions of separation gels of different concentrations (Table 2). The prepared separation gel was injected smoothly and evenly into the pre-set gel plate, paying attention to avoid the generation of air bubbles. The gel was pressed with isopropyl alcohol and allowed to stand for about 40 min, shaken gently to confirm that the colloid was solidified, then isopropyl alcohol was discarded and the gel plate was rinsed gently with double-distilled water and air-dried. The prepared upper stacking gel was added and a comb was quickly inserted vertically (Table 3). This step especially should avoid the generation of air bubbles, otherwise the sample well deformation and sample leakage might easily occur.

TABLE 2

Preparation of 10 mL SDS-PAGE separation gel components of different concentrations (mL)

| Component | 6% | 8% | 10% | 12% | 15% |
|---|---|---|---|---|---|
| Double-distilled water | 4.0 | 3.3 | 4.0 | 2.0 | 1.0 |
| 30% Acr-Bis | 2.0 | 2.7 | 5.0 | 4.0 | 5.0 |
| 1.5M Tris, pH = 8.8 | 4.8 | 3.8 | 5.7 | 3.8 | 3.8 |
| 10% SDS | 0.1 | 0.1 | 0.15 | 0.1 | 0.1 |

TABLE 2-continued

| Preparation of 10 mL SDS-PAGE separation gel components of different concentrations (mL) | | | | | |
|---|---|---|---|---|---|
| Component | 6% | 8% | 10% | 12% | 15% |
| AP | 0.1 | 0.1 | 0.15 | 0.1 | 0.1 |
| TEMED | 0.008 | 0.004 | 0.006 | 0.004 | 0.06 |

TABLE 3

| Proportion scheme for preparing 8 mL upper layer stacking gel | |
|---|---|
| Component | Volume (mL) |
| Double-distilled water | 5.5 |
| 30% Acr-Bis | 1.3 |
| 1M Tris, pH = 6.8 | 1.0 |
| 10% SDS | 0.08 |
| AP | 0.08 |
| TEMED | 0.008 |

9. TMED8 May Regulate the Biological Functions of PAAD Tumor Cells Through the MAPK Pathway and Affect the Occurrence and Development of Pancreatic Cancer PANC-1 control and overexpression cell lines (each group had 3 replicate samples) were selected for transcriptome sequencing. Through data analysis, 248 differential genes were obtained, of which 103 were up-regulated and 145 were down-regulated. These genes were visualized using heat maps and volcano plots separately, and functional annotation and KEGG enrichment analysis were performed. The MAPK signaling pathway with significant correlation was selected for further research, and the expression levels of key molecules ERK, JNK, P38 and their phosphorylation were verified by WB.

The results are shown in FIG. 9. TMED8 gene inhibited the activation of the MAPK signaling pathway.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. An overexpression plasmid of the TMED8 gene comprising a nucleotide sequence of SEQ ID NO:5.

* * * * *

SEQUENCE LISTING

```
Sequence total quantity: 5
SEQ ID NO: 1            moltype = DNA  length = 18
FEATURE                 Location/Qualifiers
source                  1..18
                        mol_type = other DNA
                        organism = synthetic construct
SEQUENCE: 1
ccacctctga tggctcct                                                18

SEQ ID NO: 2            moltype = DNA  length = 18
FEATURE                 Location/Qualifiers
source                  1..18
                        mol_type = other DNA
                        organism = synthetic construct
SEQUENCE: 2
ctcaccacgc ttcaccac                                                18

SEQ ID NO: 3            moltype = DNA  length = 20
FEATURE                 Location/Qualifiers
source                  1..20
                        mol_type = other DNA
                        organism = synthetic construct
SEQUENCE: 3
ggagcctgcg gcttaatttg                                              20

SEQ ID NO: 4            moltype = DNA  length = 20
FEATURE                 Location/Qualifiers
source                  1..20
                        mol_type = other DNA
                        organism = synthetic construct
SEQUENCE: 4
ccacccacgg aatcgagaaa                                              20

SEQ ID NO: 5            moltype = DNA  length = 9244
FEATURE                 Location/Qualifiers
source                  1..9244
                        mol_type = other DNA
                        organism = synthetic construct
SEQUENCE: 5
acgcgtgtag tcttatgcaa tactcttgta gtcttgcaac atggtaacga tgagttagca  60
acatgcctta caaggagaga aaaagcaccg tgcatgccga ttggtggaag taaggtggta  120
cgatcgtgcc ttattaggaa ggcaacagac gggtctgaca tggattggac gaaccactga  180
attgccgcat tgcagagata ttgtatttaa gtgcctagct cgatacaata aacgggtctc  240
tctggttaga ccagatctga gcctgggagc tctctggcta actagggaac ccactgctta  300
agcctcaata aagcttgcct tgagtgcttc aagtagtgtg tgcccgtctg ttgtgtgact  360
ctggtaacta gagatccctc agaccctttt agtcagtgtg gaaaatctct agcagtggcg  420
cccgaacagg gacctgaaag cgaaagggaa accagagctc tctcgacgca ggactcggct  480
tgctgaagcg cgcacggcaa gaggcgaggg gcggcgactg gtgagtacgc caaaaatttt  540
```

-continued

```
gactagcgga ggctagaagg agagagatgg gtgcgagagc gtcagtatta agcgggggag  600
aattagatcg cgatgggaaa aaattcggtt aaggccaggg ggaaagaaaa aatataaatt  660
aaaacatata gtatgggcaa gcagggagct agaacgattc gcagttaatc ctggcctgtt  720
agaaacatca gaaggctgta gacaaatact gggacagcta caaccatccc ttcagacagg  780
atcagaagaa cttagatcat tatataatac agtagcaacc ctctattgtg tgcatcaaag  840
gatagagata aaagacacca aggaagcttt agacaagata gaggaagagc aaaacaaaag  900
taagaccacc gcacagcaag cggccactga tcttcagacc tggaggagga gatatgaggg  960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggttaacttt  1800
taaaagaaaa ggggggattg gggggtacag tgcaggggaa agaatagtag acataatagc  1860
aacagacata caaactaaag aattacaaaa acaaattaca aaaattcaaa attttatcga  1920
tactagtatt atgcccagta catgacctta tgggactttc ctacttggca gtacatctac  1980
gtattagtca tcgctattac catggtgatg cggttttggc agtacatcaa tgggcgtgga  2040
tagcggtttg actcacgggg atttccaagt ctccacccca ttgacgtcaa tgggagtttg  2100
ttttggcacc aaaatcaacg ggactttcca aaatgtcgta acaactccgc cccattgacg  2160
caaatgggcg gtaggcgtgt acggtgggag gtctatataa gcagagctcg tttagtgaac  2220
cgtcagatcg cctggagacg ccatccacgc tgttttgacc tccatagaag attctagagc  2280
tagcgaattc gccaccatgt ctgacctgca ggcggctgag gggccgggct cctggagccc  2340
cacagcccgc ccagggtcgg ctggcggcgt cggggactgc cagggagtgg aggggagcca  2400
ggcggccgcc tcagagaatg aagatctaga aaacaaggat acctctttat tggcttctgc  2460
caccgatcca gaaccctgct cctcacccca caggccacag atggtatctc cagtgagtaa  2520
ggatgccacg gaagatctgc ggaaagcaac tggtcctttg gaggctcagg ccttggtgaa  2580
acaggatttg ctgcctgcag accaggccca ggtcctcaat gagagttctg ttgtgcagat  2640
ggctaagtat caagttccac agaggtctgg ggacatcgtt atgatccagt ctgaacatac  2700
aggagctata gatgttcttt cagctgattt ggaatctgca gatcttctgg gggaccacag  2760
gaaagtctcc ccacctctga tggctcctcc atgcatctgg acctttgcca aggtgaagga  2820
attcaaaagc aagctgggca aagagaagaa cagccgtctg gtggtgaagc gtggtgaggt  2880
ggtgaccatc cgggtaccta ctcatccaga ggggaagcgt gtctgctggg agtttgcgac  2940
cgatgactat gacattggct ttggagttta ttttgactgg acccctgtaa ctagcactga  3000
cataactgtg caggtcagtg attccagtga cgatgaggat gaagaagagg aagaggagga  3060
agagattgaa gaacccgttc cagctggaga tgtggagaga ggctccagga gctccttgcg  3120
gggtcgctat ggggaggtca tgcctgtgta ccggcgggac agccaccgag acgtgcaggc  3180
tggcagccat gactaccctg gtgagggcat ctacctgctc aagttcgaca actcctactc  3240
cctgctgcgc aacaagactc tctacttcca catctactac accagcggat ccgactacaa  3300
agaccatgac ggtgattata aagatcatga catcgactac aaggatgacg atgacaagtg  3360
agcggccgcg aaggatctgc gatcgctccg gtgcccgtca gtgggcagag cgcacatcgc  3420
ccacagtccc cgagaagttg gggggagggg tcggcaattg aacgggtgcc tagagaaggt  3480
ggcgcggggt aaactgggaa agtgatgtcg tgtactggct ccgccttttt cccgagggtg  3540
ggggagaacc gtatataagt gcagtagtcg ccgtgaacgt tctttttcgc aacgggtttg  3600
ccgccagaac acagctgaag cttcgagggg ctcgcatctc tccttcacgc gcccgccgcc  3660
ctacctgagg ccgccatcca cgccggttga gtcgcgttct gccgcctccc gcctgtggtg  3720
cctcctgaac tgcgtccgcc gtctaggtaa gtttaaagct caggtcgaga ccgggccttt  3780
gtccggcgct cccttggagc ctacctagac tcagccggct ctccacgctt tgcctgaccc  3840
tgcttgctca actctacgtc tttgtttcgt tttctgttct gcgccgttac agatccaagc  3900
tgtgaccggc gcctacgcta gacgccacca tggagagcga cgagagcggc ctgcccgcca  3960
tggagatcga gtgccgcatc accggcaccc tgaacggcgt ggagttcgag ctggtgggcg  4020
gcggagaggg cacccccaag cagggccgca tgaccaacaa gatgaagagc accaaaggcg  4080
ccctgacctt cagcccctac ctgctgagcc acgtgatggg ctacggcttc taccacttcg  4140
gcacctaccc cagcggctac gagaacccct tcctgcacgc catcaacaac ggcggctaca  4200
ccaacacccg catcgagaag tacgaggacg gcggcgtgct gcacgtgagc ttcagctacc  4260
gctacgaggc cggccgcgtg atcggcgact tcaaggtggt gggcaccggc ttccccgagg  4320
acagcgtgat cttcaccgac aagatcatcc gcagcaacgc caccgtggag cacctgcacc  4380
ccatgggcga taacgtgctg gtgggcagct tcgcccgcac cttcagcctg cgcgacggcg  4440
gctactacag cttcgtggtg gacagccaca tgcacttcaa gagcgccatc caccccagca  4500
tcctgcagaa cgggggcccc atgttcgcct tccgccgcgt ggaggagctg cacagcaaca  4560
ccgagctggg catcgtggag taccagcacg ccttcaagac ccccatcgcc ttcgccagat  4620
cccgcgctca gtcgtccaat tctgccgtgg acggcaccgc cggacccggc tccaccggat  4680
ctcgcgaggg cagaggaagt cttctaacat gcggtgacgt ggaggagaat cccggcccta  4740
tgaccgagta caagcccacg gtgcgcctcg ccacccgcga cgacgtcccc agggccgtac  4800
gcaccctcgc cgccgcgttc gccgactacc ccgccacgcg ccacaccgtc gatccggacc  4860
gccacatcga gcgggtcacc gagctgcaag aactcttcct cacgcgcgtc gggctcgaca  4920
tcggcaaggt gtgggtcgcg gacgacggcg ccgcggtggc ggtctggacc acgccggaga  4980
gcgtcgaagc gggggcggtg ttcgccgaga tcggcccgcg catggccgag ttgagcggtt  5040
cccggctggc cgcgcagcaa cagatggaag gcctcctggc gccgcaccgg cccaaggagc  5100
ccgcgtggtt cctggccacc gtcggcgtct cgcccgacca ccagggcaag ggtctgggca  5160
gcgccgtcgt gctccccgga gtggaggcgg ccgagcgcgc cggggtgccc gccttcctgg  5220
agacctccgc gccccgcaac ctccccttct acgagcggct cggcttcacc gtcaccgccg  5280
```

-continued

```
acgtcgaggt gcccgaagga ccgcgcacct ggtgcatgac ccgcaagccc ggtgcctgaa  5340
atcaacctct ggattacaaa atttgtgaaa gattgactgg tattcttaac tatgttgctc  5400
cttttacgct atgtggatac gctgctttaa tgcctttgta tcatgctatt gcttcccgta  5460
tggctttcat tttctcctcc ttgtataaat cctggttgct gtctctttat gaggagttgt  5520
ggcccgttgt caggcaacgt ggcgtggtgt gcactgtgtt tgctgacgca acccccactg  5580
gttggggcat tgccaccacc tgtcagctcc tttccgggac tttcgctttc cccctcccta  5640
ttgccacggc ggaactcatc gccgcctgcc ttgcccgctg ctggacaggg gctcggctgt  5700
tgggcactga caattccgtg gtgttgtcgg ggaagctgac gtcctttcca tggctgctcg  5760
cctgtgttgc cacctggatt ctgcgcggga cgtccttctg ctacgtccct tcggccctca  5820
atccagcgga ccttccttcc cgcggcctgc tgccggctct gcggcctctt ccgcgtctcc  5880
gccttcgccc tcagacgagt cggatctccc tttggccgcc tccccgcctg gtacctttaa  5940
gaccaatgac ttacaaggca gctgtagatc ttagccactt tttaaaagaa aaggggggac  6000
tggaagggct aattcactcc caacgaaaat aagatctgct ttttgcttgt actgggtctc  6060
tctggttaga ccagatctga gcctgggagc tctctggcta actagggaac ccactgctta  6120
agcctcaata aagcttgcct tgagtgcttc aagtagtgtg tgcccgtctg ttgtgtgact  6180
ctggtaacta gagatccctc agaccctttt agtcagtgtg gaaaatctct agcagtagta  6240
gttcatgtca tcttattatt cagtatttat aacttgcaaa gaaatgaata tcagagagtg  6300
agaggaactt gtttattgca gcttataatg gttacaaata aagcaatagc atcacaaatt  6360
tcacaaataa agcatttttt tcactgcatt ctagttgtgg tttgtccaaa ctcatcaatg  6420
tatcttatca tgtctggctc tagctatccc gcccctaact ccgcccagtt ccgcccattc  6480
tccgccccat ggctgactaa ttttttttat ttatgcagag gccgaggccg cctcggcctc  6540
tgagctattc cagaagtagt gaggaggctt ttttggaggc ctagactttt gcagagacgg  6600
cccaaattcg taatcatggt catagctgtt tcctgtgtga aattgttatc cgctcacaat  6660
tccacacaac atacgagccg gaagcataaa gtgtaaagcc tggggtgcct aatgagtgag  6720
ctaactcaca ttaattgcgt tgcgctcact gcccgctttc cagtcgggaa acctgtcgtg  6780
ccagctgcat taatgaatcg gccaacgcgc ggggagaggc ggtttgcgta ttgggcgctc  6840
ttccgcttcc tcgctcactg actcgctgcg ctcggtcgtt cggctgcggc gagcggtatc  6900
agctcactca aaggcggtaa tacggttatc cacagaatca ggggataacg caggaaagaa  6960
catgtgagca aaaggccagc aaaaggccag gaaccgtaaa aaggccgcgt tgctggcgtt  7020
tttccatagg ctccgccccc ctgacgagca tcacaaaaat cgacgctcaa gtcagaggtg  7080
gcgaaacccg acaggactat aaagatacca ggcgtttccc cctggaagct ccctcgtgcg  7140
ctctcctgtt ccgaccctgc cgcttaccgg atacctgtcc gcctttctcc cttcgggaag  7200
cgtggcgctt tctcatagct cacgctgtag gtatctcagt tcggtgtagg tcgttcgctc  7260
caagctgggc tgtgtgcacg aaccccccgt tcagcccgac cgctgcgcct tatccggtaa  7320
ctatcgtctt gagtccaacc cggtaagaca cgacttatcg ccactggcag cagccactgg  7380
taacaggatt agcagagcga ggtatgtagg cggtgctaca gagttcttga agtggtggcc  7440
taactacggc tacactagaa ggacagtatt tggtatctgc gctctgctga agccagttac  7500
cttcggaaaa agagttggta gctcttgatc cggcaaacaa accaccgctg gtagcggtgg  7560
tttttttgtt tgcaagcagc agattacgcg cagaaaaaaa ggatctcaag aagatccttt  7620
gatcttttct acggggtctg acgctcagtg gaacgaaaac tcacgttaag ggattttggt  7680
catgagatta tcaaaaagga tcttcaccta gatcctttta aattaaaaat gaagttttaa  7740
atcaatctaa agtatatatg agtaaacttg gtctgacagt taccaatgct taatcagtga  7800
ggcacctatc tcagcgatct gtctatttcg ttcatccata gttgcctgac tccccgtcgt  7860
gtagataact acgatacggg agggcttacc atctggcccc agtgctgcaa tgataccgcg  7920
agacccacgc tcaccggctc cagatttatc agcaataaac cagccagccg gaagggccga  7980
gcgcagaagt ggtcctgcaa ctttatccgc ctccatccag tctattaatt gttgccggga  8040
agctagagta agtagttcgc cagttaatag tttgcgcaac gttgttgcca ttgctacagg  8100
catcgtggtg tcacgctcgt cgtttggtat ggcttcattc agctccggtt cccaacgatc  8160
aaggcgagtt acatgatccc ccatgttgtg caaaaaagcg gttagctcct tcggtcctcc  8220
gatcgttgtc agaagtaagt tggccgcagt gttatcactc atggttatgg cagcactgca  8280
taattctctt actgtcatgc catccgtaag atgcttttct gtgactggtg agtactcaac  8340
caagtcattc tgagaatagt gtatgcggcg accgagttgc tcttgcccgg cgtcaatacg  8400
ggataatacc gcgccacata gcagaacttt aaaagtgctc atcattggaa aacgttcttc  8460
ggggcgaaaa ctctcaagga tcttaccgct gttgagatcc agttcgatgt aacccactcg  8520
tgcacccaac tgatcttcag catcttttac tttcaccagc gtttctgggt gagcaaaaac  8580
aggaaggcaa aatgccgcaa aaaagggaat aagggcgaca cggaaatgtt gaatactcat  8640
actcttcctt tttcaatatt attgaagcat ttatcagggt tattgtctca tgagcggata  8700
catatttgaa tgtatttaga aaaataaaca aataggggtt ccgcgcacat ttccccgaaa  8760
agtgccacct gacgtctaag aaaccattat tatcatgaca ttaacctata aaaataggcg  8820
tatcacgagg ccctttcgtc tcgcgcgttt cggtgatgac ggtgaaaacc tctgacacat  8880
gcagctcccg gagacggtca cagcttgtct gtaagcggat gccgggagca gacaagcccg  8940
tcagggcgcg tcagcgggtg ttggcgggtg tcggggctgg cttaactatg cggcatcaga  9000
gcagattgta ctgagagtgc accatatgcg gtgtgaaata ccgcacagat gcgtaaggag  9060
aaaataccgc atcaggcgcc attcgccatt caggctgcgc aactgttggg aagggcgatc  9120
ggtgcgggcc tcttcgctat tacgccagct ggcgaaaggg ggatgtgctg caaggcgatt  9180
aagttgggta acgccagggt tttcccagtc acgacgttgt aaaacgacgg ccagtgccaa  9240
gctg                                                               9244
```